(12) United States Patent
Vega García et al.

(10) Patent No.: US 11,466,012 B2
(45) Date of Patent: Oct. 11, 2022

(54) TETRAHYDROISOQUINOLINE COMPOUNDS

(71) Applicant: ALLINKY BIOPHARMA, Madrid (ES)

(72) Inventors: Miguel Vega García, Madrid (ES); Pedro Campos Muelas, Madrid (ES); Esther Carrasco Romero, Madrid (ES); Asunción Burguete Pérez, Madrid (ES); Patricia Gómez Gutiérrez, Madrid (ES); Juan Jesús Pérez González, Madrid (ES); Ángel Messeguer Peypoch, Madrid (ES); Balbino José Alarcón Sánchez, Madrid (ES); Irene Azahara Arellano Rojo, Madrid (ES)

(73) Assignee: ALLINKY BIOPHARMA, Madrid (ES)

( * ) Notice: Subject to any disclaimer, the term of this patent is extended or adjusted under 35 U.S.C. 154(b) by 0 days.

(21) Appl. No.: 16/961,190

(22) PCT Filed: Jan. 10, 2019

(86) PCT No.: PCT/EP2019/050518
§ 371 (c)(1),
(2) Date: Jul. 9, 2020

(87) PCT Pub. No.: WO2019/137985
PCT Pub. Date: Jul. 18, 2019

(65) Prior Publication Data
US 2020/0369671 A1    Nov. 26, 2020

(30) Foreign Application Priority Data
Jan. 10, 2018 (EP) .................... 18382010

(51) Int. Cl.
*C07D 401/12* (2006.01)
*C07D 413/12* (2006.01)
*C07D 413/14* (2006.01)
*C07D 217/12* (2006.01)
*C07D 487/04* (2006.01)

(52) U.S. Cl.
CPC ......... *C07D 487/04* (2013.01); *C07D 217/12* (2013.01); *C07D 401/12* (2013.01); *C07D 413/12* (2013.01); *C07D 413/14* (2013.01)

(58) Field of Classification Search
CPC ... C07D 413/12; C07D 413/14; C07D 217/12
See application file for complete search history.

(56) References Cited

U.S. PATENT DOCUMENTS 8,293,911 B2   10/2012 Vernier et al.
2010/0249115 A1   9/2010 Nicewonger et al.
2022/0002276 A1   1/2022 Vega et al.

FOREIGN PATENT DOCUMENTS

| JP | 5419691 B2 | 11/2013 |
| WO | 00/78708 A1 | 12/2000 |
| WO | 2009/055077 A1 | 4/2009 |
| WO | 2011/017125 A1 | 2/2011 |
| WO | 2015/089337 A1 | 6/2015 |
| WO | 2016/033105 A1 | 3/2016 |

OTHER PUBLICATIONS

Gitto et al. IL FARMACO, 2004, vol. 59, pp. 7-12.*
Golub et al., Science, vol. 286, Oct. 15, 1999, pp. 531-537.*
De Los Angeles et al., "Iodinated Analogs of Trimetoquinol as Highly Potent and Selective β2-Adrenoceptor Ligands," *J Med. Chem.* 39(19):3701-3711, 1996.
Fodor et al., "The Mechanism of the Bischler-Napieralski Reaction," *Angew. Chem. Internat. Edit.* 11(10): 919-920, 1972.
Gitto et al., "Discovery of a Novel and Highly Potent Noncompetitive AMPA Receptor Antagonist," *J. Med. Chem.* 46(1):197-200, 2003.
Liu et al., "Discovery of Potent, Selective, Orally Bioavailable Stearoyl-CoA Desaturase 1 Inhibitors," *J. Med. Chem* 50(13):3086-3100, 2007.
Marin-Ramos et al., "Blocking Ras inhibition as an antitumor strategy," *Seminars in Cancer Biology* 54:91-100, 2018, Retrieved from https://doi.org/10.1016/j.semcancer.2018.01.017.
Xie et al., "Identification of a New Potent Inhibitor Targeting KRAS in Non-small Cell Lung Cancer Cells," *Frontiers in Pharmacology* 8(823):1-8, 2017.
Yokoyama et al., "Prototype Pictet-Spengler Reactions Catalyzed by Superacids. Involvement of Dicationic Superelectrophiles," *J. Org. Chem.* 64(2):611-617, 1999.

* cited by examiner

*Primary Examiner* — Samira J Jean-Louis
(74) *Attorney, Agent, or Firm* — Seed IP Law Group LLP

(57) ABSTRACT

The present invention relates to a novel class of tetrahydroisoquinoline compounds of formula I and to compositions comprising the same. The compounds and compositions of the present invention can be used as medicaments in the treatment of cancer.

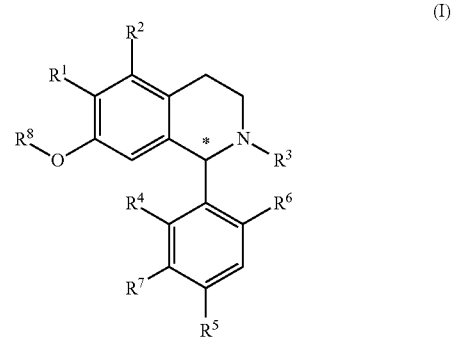

(I)

14 Claims, 1 Drawing Sheet

TETRAHYDROISOQUINOLINE COMPOUNDS

FIELD OF THE INVENTION

Figure 1:
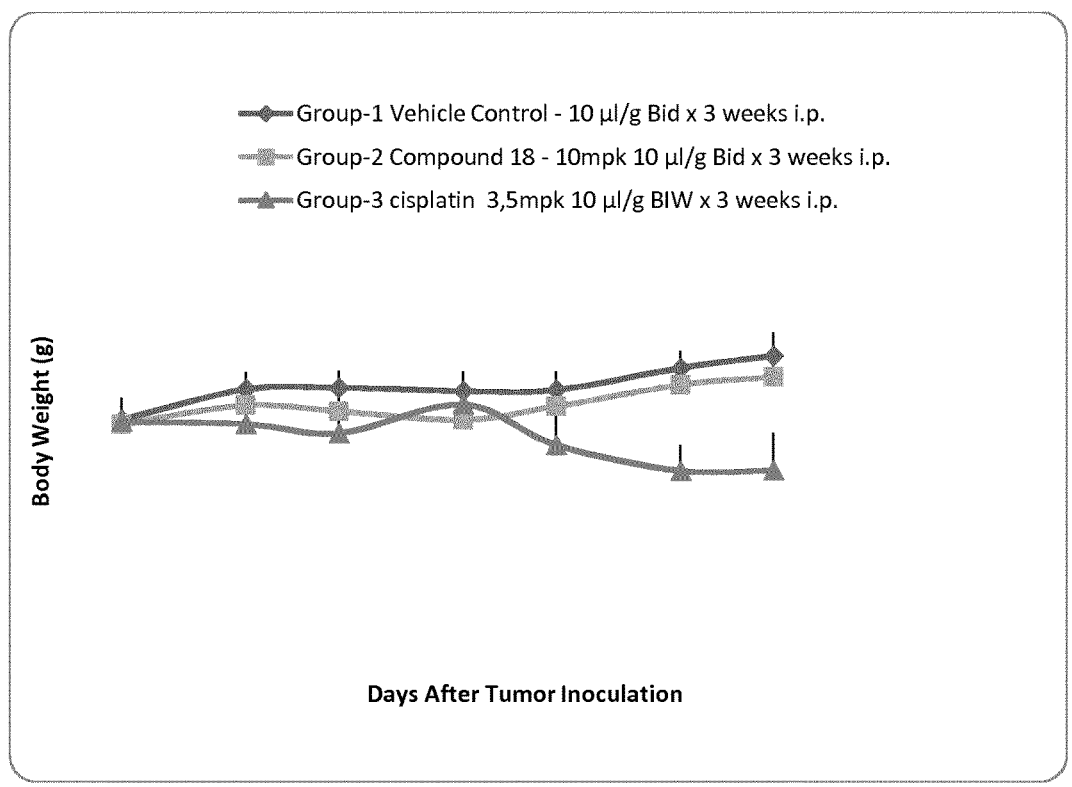

The present invention relates to a novel class of tetrahydroisoquinoline compounds and to compositions comprising the same. The compounds and compositions (such as pharmaceutical compositions) of the present invention can be used as medicaments in the treatment of cancer.

BACKGROUND OF THE INVENTION

Cancer genome sequencing efforts over the past 10 to 15 years have led to the identification of numerous oncogenes responsible for the development and maintenance of human cancer. Despite the identification of more than 500 validated cancer genes the three RAS genes HRAS, NRAS and KRAS still constitute the most frequently mutated oncogene family in human cancer.

When RAS is 'switched on' by incoming signals, it subsequently switches on other proteins, which ultimately turn on genes involved in cell growth, differentiation and survival. Mutations in ras genes can lead to the production of permanently activated RAS proteins. As a result, this can cause unintended and overactive signaling inside the cell, even in the absence of incoming signals.

Because these signals result in cell growth and division, overactive RAS signaling can ultimately lead to cancer. The 3 RAS genes (HRas, KRas, and NRas) are the most common oncogenes in human cancer; mutations that permanently activate RAS are found in 20% to 25% of all human tumors and up to 90% in certain types of cancer.

Cancers harboring RAS mutations remained essentially untreatable more than 30 years after the initial discovery of the oncogene. Thus, for many years RAS was considered to be "undruggable".

Among HRAS, NRAS and KRAS, KRAS is the most frequently mutated RAS isoform having been shown to be mutated in 90% of pancreatic adenocarcinoma, 45% of colon rectal cancers and 35% of lung adenocarcinoma. KRAS mutations have been associated with increased tumorigenicity and poor prognosis.

To date, different types of drugs are used as anticancer drugs and cisplatin represents one of the most popular. Cisplatin is used to treat various types of cancers, including sarcomas, some carcinomas (e.g., small cell lung cancer, squamous cell carcinoma of the head and neck and ovarian cancer), lymphomas, bladder cancer, cervical cancer and germ cell tumors. Even though it resulted to be very effective in some kinds of cancer (such as testicular cancer) it shows a number of side-effects that can limit its use. Furthermore, according to the mechanism of action proposed for cisplatin, it should interfere with DNA replication, killing the fastest proliferating cells, which in theory are carcinogenic. However, cisplatin is not really selective towards carcinogenic cells.

Thus, there is still a need to provide novel compounds acting as anti-cancer drugs and, at the same time, having low toxicity.

SUMMARY OF THE INVENTION

The present invention provides a novel class of compounds having Formula I and/or Formula II, which includes enantiomers and pharmaceutically acceptable salts thereof. The compounds of the present invention selectively and effectively inhibit RAS proteins, and particularly KRAS proteins, thereby representing excellent anti-cancer drugs useful in the treatment of a variety of cancers, such as large intestine cancer, colon cancer, rectal cancer, pancreatic cancer, breast cancer, multiple myeloma, leukemia and lung cancer. Compared to known compounds used in the treatment of cancer, the compounds of the present invention also exhibit lower toxicity.

The compounds of the present invention are compounds of Formula I, enantiomers or pharmaceutically acceptable salts thereof:

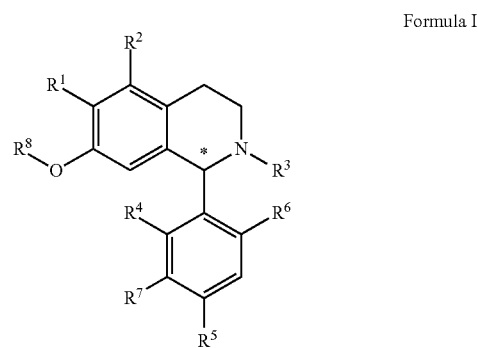

Formula I wherein $R^1$ is $(R^y)_k{}^1{-}(Y^1)_n{}^1{-}(X^1)_m{}^1{-}R^x$, $(R^y)_k{}^1{-}(X^1)_m{}^1{-}(Y^1)_n{}^1{-}R^x$ or halogen such as $OR^x$ or $Y^1X^1R^x$, more particularly $OR^x$, $Y^1$ is $C(O)$ or $S(O)_2$, such as $C(O)$, $X^1$ is NH or O, $R^y$ is $C_{1-4}$ alkanediyl, $C_{2-4}$ alkenediyl, or $C_{2-4}$ alkynediyl, such as $-CH_2-$, $R^x$ is $C_{1-4}$ alkyl, $C_{2-4}$ alkenyl, $C_{2-4}$ alkynyl, or H, such as $CH_3$ or H;

$k^1$ is 0 or 1, $n^1$ is 0 or 1, $m^1$ is 0 or 1, $R^2$ is H, $C_{1-4}$ alkyl, $C_{2-4}$ alkenyl, $C_{2-4}$ alkynyl, halogen, $OC_{1-4}$ alkyl, $OC_{2-4}$ alkenyl, or $OC_{2-4}$ alkynyl, such as H, $CH_3$, or $OCH_3$, particularly H or $OCH_3$, more particularly H;

$R^3$ is $-(CH_2)_n{}^3{-}C(Y^3){-}(X^3)_m{}^3{-}(CH_2)_k{}^3{-}R^{3a}$, $n^3$ is an integer in the range of 0 to 2, such as 0 or 2, $X^3$ is S, NH, or O, such as NH or O, particularly NH, $Y^3$ is S or O, such as O, $m^3$ is 0 or 1, $k^3$ is 0 or 1, $R^{3a}$ is $C_{1-4}$ alkyl, $C_{2-4}$ alkenyl, $C_{2-4}$ alkynyl, $OC_{1-4}$ alkyl, $OC_{2-4}$ alkenyl, $OC_{2-4}$ alkynyl, $Het^3$, $Ar^3$, $HetCyc^3$ or $Cyc^3$, such as $C_{1-4}$ alkyl or $Het^3$, $Het^3$ is a 5- to 10-membered heteroaromatic ring or ring system containing one or more heteroatoms selected from the group consisting of N, O, and S, such as oxazolyl, thiazolyl, or pyridinyl, particularly oxazol-4-yl, thiazol-4-yl, or pyridin-4-yl, $Ar^3$ is a 6- to 10-membered aromatic ring or ring system, such as phenyl or naphtyl, $HetCyc^3$ is a 3- to 8-membered heterocyclyl containing one or more heteroatoms selected from the group consisting of N, O, and S, such as pyrrolidinyl, oxazolidinyl, morpholinyl, $Cyc^3$ is a 3- to 8-membered cyclyl, such as cyclopropyl, cyclobutyl, cyclopentyl, cyclohexyl, cycloheptyl or cyclooctyl;

$R^4$ is halogen, $OC_{1-4}$ alkyl, $OC_{2-4}$ alkenyl, $OC_{2-4}$ alkynyl, $C_{1-4}$ alkyl, $C_{2-4}$ alkenyl or $C_{2-4}$ alkynyl, such as halogen or $C_{1-2}$ alkyl, particularly Cl, F, or $C_{1-2}$ alkyl, more particularly, Cl, F, or $CH_3$, even more particularly Cl or $CH_3$, such as $CH_3$;

$R^5$ is hydrogen, $OC_{1-4}$ alkyl, $OC_{2-4}$ alkenyl, $OC_{2-4}$ alkynyl, OH, $C_{1-4}$ alkyl, $C_{2-4}$ alkenyl, or $C_{2-4}$ alkynyl, each $C_{1-4}$ alkyl, $C_{2-4}$ alkenyl, or $C_{2-4}$ alkynyl independently optionally substituted with 1 to 3 halogens, such as F, particularly H, $C_{1-2}$ alkyl, or $OC_{1-2}$ alkyl, more particularly $C_{1-2}$ alkyl or $OC_{1-2}$ alkyl, even more particularly $CH_3$ or $OCH_3$, such as $CH_3$;

$R^6$ is H, OH, halogen, or $NH_2$, such as H or OH, more particularly H;

$R^7$ is H, halogen, OH, $C_{1-4}$ alkyl, $C_{2-4}$ alkenyl, $C_{2-4}$ alkynyl, $OC_{1-4}$ alkyl, $OC_{2-4}$ alkenyl, or $OC_{2-4}$ alkynyl, such as H, $CH_3$, or $OCH_3$, particularly H or $OCH_3$, more particularly H;

$R^8$ is —$(CH_2)_{n^8}$—$(C(O))_{m^8}$—$R^{8a}$, $n^8$ is an integer from 1 to 2, such as 2, $m^8$ is an integer from 0 to 1, such as 0, and $R^{8a}$ is an aromatic or heteroaromatic ring having 5 or 6 ring members, optionally substituted with at least 1 substituent selected from the group consisting of OH, $C_{1-4}$ alkyl, $C_{2-4}$ alkenyl, $C_{2-4}$ alkynyl, $OC_{1-4}$ alkyl, $OC_{2-4}$ alkenyl, $OC_{2-4}$ alkynyl, $CO_2$—$C_{1-4}$ alkyl, $CO_2$—$C_{2-4}$ alkenyl, $CO_2$—$C_{2-4}$ alkynyl, halogen, $CONH_2$, CN, COOH, —OCO—$C_{1-4}$ alkyl, —OCO—$C_{2-4}$ alkenyl, —OCO—$C_{2-4}$ alkynyl, —NHCO—$C_{1-4}$ alkyl, —NHCO—$C_{2-4}$ alkenyl, —NHCO—$C_{2-4}$ alkynyl, $NH_2$, $NHC_{1-4}$ alkyl, $NHC_{2-4}$ alkenyl, $NHC_{2-4}$ alkynyl, $N(C_{1-4}$ alkyl$)_2$, $N(C_{2-4}$ alkenyl$)_2$, $N(C_{2-4}$ alkynyl$)_2$, $CONHC_{1-4}$ alkyl, $CONHC_{2-4}$ alkenyl, $CONHC_{2-4}$ alkynyl, $CON(C_{1-4}$ alkyl$)_2$, $CON(C_{2-4}$ alkenyl$)_2$, $CON(C_{2-4}$ alkynyl$)_2$, such as OH, OCH3, $CO_2CH3$, halogen, CONH2, CN, and COOH, particularly OH, $OCH_3$, $CO_2CH_3$, F, $CONH_2$, CN, and COOH, more particularly, OH, $OCH_3$, and F, even more particularly OH and F, such as OH; or $R^{8a}$ is an aromatic or heteroaromatic ring having 5 or 6 ring members fused with an additional optionally substituted cyclic, heterocyclic, aromatic, or heteroaromatic ring, such as an optionally substituted cyclic, heterocyclic, or heteroaromatic ring.

DETAILED DESCRIPTION OF THE INVENTION

Definitions

In the present context, the term "$C_{1-4}$ alkyl" is intended to mean a linear or branched hydrocarbon group having 1 to 4 carbon atoms, such as methyl, ethyl, n-propyl, iso-propyl, n-butyl, iso-butyl, sec-butyl, and tert-butyl.

Similarly, the term "$C_{2-4}$ alkenyl" is intended to cover linear or branched hydrocarbon groups having 2 to 4 carbon atoms and comprising a double bond. Examples of alkenyl groups are vinyl, allyl, and butenyl. Preferred examples of alkenyl are vinyl and allyl, especially allyl.

In the present context the term "$C_{2-4}$ alkynyl" is intended to mean a linear or branched hydrocarbon group having 2 to 4 carbon atoms and containing a triple bond. Illustrative examples of $C_{2-4}$ alkynyl groups include acetylene, propynyl, butynyl, as well as branched forms of these. The position of unsaturation (the triple bond) may be at any position along the carbon chain. More than one bond may be unsaturated such that the "$C_{2-4}$ alkynyl" is a di-yne as is known to the person skilled in the art.

In the present context, the term "$C_{1-4}$ alkanediyl" is intended to mean a divalent linear or branched hydrocarbon group having 1 to 4 carbon atoms, such as methanediyl, ethanediyl, propanediyl, or butanediyl.

Similarly, the term "$C_{2-4}$ alkenediyl" is intended to cover divalent linear or branched hydrocarbon groups having 2 to 4 carbon atoms and comprising a double bond.

In the present context the term "$C_{2-4}$ alkynediyl" is intended to mean a divalent linear or branched hydrocarbon group having 2 to 4 carbon atoms and containing a triple bond.

Herein, the term "halogen" includes fluoro, chloro, bromo, and iodo, more particularly, fluoro, chloro and bromo.

In the present context the term "aromatic ring or ring system" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl.

The term "heteroaromatic ring or ring system" is intended to mean a fully or partially aromatic carbocyclic ring or ring system where one or more of the carbon atoms have been replaced with heteroatoms, e.g. nitrogen (=N— or —NH—), sulphur, and/or oxygen atoms. Examples of such heteroaromatic ring or ring system groups are oxazolyl, isoxazolyl, thiazolyl, isothiazolyl, pyrrolyl, imidazolyl, pyrazolyl, pyridinyl, pyrimidinyl, pyrazinyl, pyridazinyl, triazinyl, coumaryl, furyl, thienyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl and phenoxazonyl.

In the present context, the term "heterocyclic ring or ring system" is intended to mean a non-aromatic carbocyclic ring or ring system where one or more of the carbon atoms have been replaced with heteroatoms, e.g. nitrogen (=N— or —NH—), sulphur, and/or oxygen atoms. Examples of such heterocyclic groups are imidazolidine, piperazine, hexahydropyridazine, hexahydropyrimidine, diazepane, diazocane, pyrrolidine, piperidine, azepane, azocane, aziridine, azirine, azetidine, pyroline, tropane, oxazinane (morpholine), azepine, dihydroazepine, tetrahydroazepine, hexahydroazepine, oxazolane, oxazepane, oxazocane, thiazolane, thiazinane, thiazepane, thiazocane, oxazetane, diazetane, thiazetane, tetrahydrofuran, tetrahydropyran, oxepane, tetrahydrothiophene, tetrahydrothiopyrane, thiepane, dithiane, dithiepane, dioxane, dioxepane, oxathiane and oxathiepane.

In the present context, the term "optionally substituted" is intended to mean that the group in question may be substituted at least once. Furthermore, the term "optionally substituted" may also mean that the group in question is unsubstituted.

The compounds of the present invention can be in a free form or in the form of a pharmaceutically acceptable salt. In the context of the present invention, the term "pharmaceutically acceptable salt" is to be understood as a salt formed with either a base or an acid, wherein the resulting counter-ion does not significantly add to the toxicity of the compound of the present invention.

Examples of pharmaceutically acceptable salts include inorganic acid salts such as hydrochloride, sulfate, nitrate, phosphate or hydrobromide, etc., organic acid salts such as acetate, fumarate, oxalate, citrate, methanesulfonate, benzenesulfonate, p-toluenesulfonate or maleate, etc. Also, when the compound has a substituent such as carboxyl group, there may be mentioned a salt with a base (for example, alkali metal salt such as sodium salt, potassium salt, etc. or alkaline earth metal salt such as calcium salt, etc.).

Compounds

The compounds of the invention are compounds of Formula I, enantiomers or pharmaceutically acceptable salts thereof:

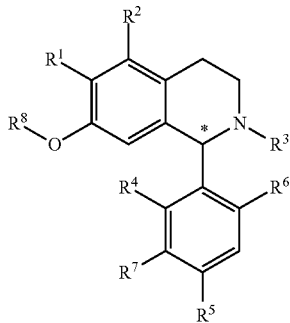

Formula I wherein $R^1$ is $(R^y)_k^1$—$(Y^1)_n^1$—$(X^1)_m^1$—$R^x$, $(R^y)_k^1$—$(X^1)_m^1$—$(Y^1)_n^1$—$R^x$ or halogen such as $OR^x$ or $Y^1X^1R^x$, more particularly $OR^x$, $Y^1$ is C(O) or $S(O)_2$, such as C(O), $X^1$ is NH or O, $R^y$ is $C_{1-4}$ alkanediyl, $C_{2-4}$ alkenediyl, or $C_{2-4}$ alkynediyl, such as —$CH_2$—, $R^x$ is $C_{1-4}$ alkyl, $C_{2-4}$ alkenyl, $C_{2-4}$ alkynyl, or H, such as $CH_3$ or H;

$k^1$ is 0 or 1, $n^1$ is 0 or 1, $m^1$ is 0 or 1, $R^2$ is H, $C_{1-4}$ alkyl, $C_{2-4}$ alkenyl, $C_{2-4}$ alkynyl, halogen, $OC_{1-4}$ alkyl, $OC_{2-4}$ alkenyl, or $OC_{2-4}$ alkynyl, such as H, $CH_3$, or $OCH_3$, particularly H or $OCH_3$, more particularly H;

$R^3$ is —$(CH_2)_n^3$—$C(Y^3)$—$(X^3)_m^3$—$(CH_2)_k^3$—$R^{3a}$, $n^3$ is an integer in the range of 0 to 2, such as 0 or 2, $Y^3$ is S or O, such as O, $X^3$ is S, NH, or O, such as NH or O, particularly NH, $m^3$ is 0 or 1, $k^3$ is 0 or 1, $R^{3a}$ is $C_{1-4}$ alkyl, $C_{2-4}$ alkenyl, $C_{2-4}$ alkynyl, $OC_{1-4}$ alkyl, $OC_{2-4}$ alkenyl, $OC_{2-4}$ alkynyl, $Het^3$, $Ar^3$, $HetCyc^3$ or $Cyc^3$, such as $C_{1-4}$ alkyl or $Het^3$, $Het^3$ is a 5- to 10-membered heteroaromatic ring or ring system containing one or more heteroatoms selected from the group consisting of N, O, and S, such as oxazolyl, thiazolyl, or pyridinyl, particularly oxazol-4-yl, thiazol-4-yl, or pyridin-4-yl, $Ar^3$ is a 6- to 10-membered aromatic ring or ring system, such as phenyl or naphthyl, $HetCyc^3$ is a 3- to 8-membered heterocyclyl containing one or more heteroatoms selected from the group consisting of N, O, and S, such as pyrrolidinyl, oxazolidinyl, morpholinyl, $Cyc^3$ is a 3- to 8-membered cyclyl, such as cyclopropyl, cyclobutyl, cyclopentyl, cyclohexyl, cycloheptyl or cyclooctyl;

$R^4$ is halogen, $OC_{1-4}$ alkyl, $OC_{2-4}$ alkenyl, $OC_{2-4}$ alkynyl, $C_{1-4}$ alkyl, $C_{2-4}$ alkenyl or $C_{2-4}$ alkynyl, such as halogen or $C_{1-2}$ alkyl, particularly Cl, F or $C_{1-2}$ alkyl, more particularly, Cl, F, or $CH_3$, even more particularly Cl or $CH_3$, such as $CH_3$;

$R^5$ is hydrogen, $OC_{1-4}$ alkyl, $OC_{2-4}$ alkenyl, $OC_{2-4}$ alkynyl, OH, $C_{1-4}$ alkyl, $C_{2-4}$ alkenyl, or $C_{2-4}$ alkynyl, each $C_{1-4}$ alkyl, $C_{2-4}$ alkenyl, or $C_{2-4}$ alkynyl independently optionally substituted with 1 to 3 halogens, such as F, particularly H, $C_{1-2}$ alkyl, or $OC_{1-2}$ alkyl, more particularly $C_{1-2}$ alkyl or $OC_{1-2}$ alkyl, even more particularly $CH_3$ or $OCH_3$, such as $CH_3$, $R^6$ is H, OH, halogen, or $NH_2$, such as H or OH, more particularly H;

$R^7$ is H, halogen, OH, $C_{1-4}$ alkyl, $C_{2-4}$ alkenyl, $C_{2-4}$ alkynyl, $OC_{1-4}$ alkyl, $OC_{2-4}$ alkenyl, or $OC_{2-4}$ alkynyl, such as H, $CH_3$, or $OCH_3$, particularly H or $OCH_3$, more particularly H;

$R^8$ is —$(CH_2)_n^8$—$(C(O))_m^8$—$R^{8a}$, $n^8$ is an integer from 1 to 2, such as 2

$m^8$ is an integer from 0 to 1, such as 0, and $R^{8a}$ is an aromatic or heteroaromatic ring having 5 or 6 ring members, optionally substituted with at least 1 substituent selected from the group consisting of OH, $C_{1-4}$ alkyl, $C_{2-4}$ alkenyl, $C_{2-4}$ alkynyl, $OC_{1-4}$ alkyl, $OC_{2-4}$ alkenyl, $OC_{2-4}$ alkynyl, $CO_2$—$C_{1-4}$ alkyl, $CO_2$—$C_{2-4}$ alkenyl, $CO_2$—$C_{2-4}$ alkynyl, halogen, $CONH_2$, CN, COOH, —OCO—$C_{1-4}$ alkyl, —OCO—$C_{2-4}$ alkenyl, —OCO—$C_{2-4}$ alkynyl, —NHCO—$C_{1-4}$ alkyl, —NHCO—$C_{2-4}$ alkenyl, —NHCO—$C_{2-4}$ alkynyl, $NH_2$, $NHC_{1-4}$ alkyl, $NHC_{2-4}$ alkenyl, $NHC_{2-4}$ alkynyl, $N(C_{1-4}$ alkyl$)_2$, $N(C_{2-4}$ alkenyl$)_2$, $N(C_{2-4}$ alkynyl$)_2$, $CONHC_{1-4}$ alkyl, $CONHC_{2-4}$ alkenyl, $CONHC_{2-4}$ alkynyl, $CON(C_{1-4}$ alkyl$)_2$, $CON(C_{2-4}$ alkenyl$)_2$, $CON(C_{2-4}$ alkynyl$)_2$, such as OH, $OCH_3$, $CO_2CH_3$, halogen, $CONH_2$, CN, and COOH, particularly OH, $OCH_3$, $CO_2CH_3$, F, $CONH_2$, CN, and COOH, more particularly, OH, $OCH_3$, and F, even more particularly OH and F, such as OH; or $R^{8a}$ is an aromatic or heteroaromatic ring having 5 or 6 ring members fused with an additional optionally substituted cyclic, heterocyclic, aromatic, or heteroaromatic ring, such as an optionally substituted cyclic, heterocyclic, or heteroaromatic ring.

In one embodiment, $R^{8a}$ is a phenyl ring, optionally substituted with at least 1 substituent selected from the group consisting of OH, $C_{1-4}$ alkyl, $OC_{1-4}$ alkyl, $CO_2$—$C_{1-4}$ alkyl, halogen, $CONH_2$, CN, and COOH. In another embodiment, $R^{8a}$ is a phenyl ring, optionally substituted with at least 1 substituent selected from the group consisting of OH, $OCH_3$, $CO_2CH_3$, halogen, $CONH_2$, CN, and COOH. In a further embodiment, $R^{8a}$ is a phenyl ring, optionally substituted with at least 1 substituent selected from the group consisting of OH, $OCH_3$, $CO_2CH_3$, F, $CONH_2$, CN, and COOH. In still another embodiment, $R^{8a}$ is a phenyl ring, optionally substituted with at least 1 substituent selected from the group consisting of OH, $OCH_3$, and F. In yet a further embodiment, $R^{8a}$ is a phenyl ring, optionally substituted with at least 1 substituent selected from the group consisting of OH and F. In yet another embodiment, $R^{8a}$ is a phenyl ring, optionally substituted with at least 1 OH group.

In a further embodiment, at least one substituent is in the meta position relative to the position connecting the phenyl ring to the tetrahydroisoquinoline core.

$R^{8a}$ may also be a 5 or 6-membered heteroaromatic ring, optionally substituted with at least 1 substituent selected from the group consisting of OH, $C_{1-4}$ alkyl, $OC_{1-4}$ alkyl, $CO_2$—$C_{1-4}$ alkyl, halogen, $CONH_2$, CN, and COOH, such as OH, $OCH_3$, $CO_2CH_3$, halogen, $CONH_2$, CN, and COOH, particularly OH, $OCH_3$, $CO_2CH_3$, F, $CONH_2$, CN, and COOH, more particularly, OH, $OCH_3$, and F, even more particularly OH and F, such as OH. In one embodiment, $R^{8a}$ is optionally substituted pyridinyl, indanyl, dihydro-benzofuranyl, indolinyl or triazolopyrimidinyl. In a further embodiment, $R^{8a}$ is optionally substituted pyridinyl, optionally substituted indanyl, or optionally substituted dihydrobenzofuranyl. In another embodiment, $R^{8a}$ is optionally substituted indanyl or optionally substituted pyridinyl. In yet another embodiment, $R^{8a}$ is pyridinyl.

$R^3$ is $-(CH_2)_{n^3}-C(Y^3)-(X^3)_{m^3}-(CH_2)_{k^3}-R^{3a}$. In one embodiment, $Y^3$ is O. In a further embodiment, $X^3$ is NH. In another embodiment, $Y^3$ is O and $X^3$ is NH. In a further variation of these embodiments, $n^3$ is 0. In another variation of these embodiments, $m^3$ is 1. In still another variation of these embodiments, $n^3$ is 0 and $m^3$ is 1. In yet another variation of these embodiments, $R^{3a}$ is oxazolyl or pyridinyl, such as oxazol-4-yl or pyridin-4-yl.

In a different variation of the embodiment, wherein $Y^3$ is O, $n^3$ is 2 and $m^3$ is 0.

In still a further variation of these embodiments having different variants of $R^3$, $k^3$ is 1.

$R^1$ is $(R^y)_k{}^1-(Y^1)_n{}^1-(X^1)_m{}^1-R^x$, $(R^y)_k{}^1-(X^1)_m{}^1-(Y^1)_n{}^1-R^x$ or halogen. In one embodiment, $R^1$ is $OR^x$ or $Y^1X^1R^x$. In a further embodiment, $R^1$ is $OR^x$. In still a further embodiment, $R^1$ is $OCH_3$.

$Y^1$ is $C(O)$ or $S(O)_2$. In one embodiment, $Y^1$ is $C(O)$.

$X^1$ is NH or O. In one embodiment $X^1$ is NH.

$k^1$ is 0 or 1. In one embodiment, $k^1$ is 0.

$n^1$ is 0 or 1. In one embodiment, $n^1$ is 1.

$m^1$ is 0 or 1. In one embodiment, $n^1$ is 1.

$R^x$ is $C_{1-4}$ alkyl, $C_{2-4}$ alkenyl, $C_{2-4}$ alkynyl or H. In one embodiment, $R^x$ is $CH_3$ or H.

In a further embodiment, $R^1$ is $C(O)NHR^x$.

$R^2$ is H, $C_{1-4}$ alkyl, $C_{2-4}$ alkenyl, $C_{2-4}$ alkynyl, halogen, $OC_{1-4}$ alkyl, $OC_{2-4}$ alkenyl, or $OC_{2-4}$ alkynyl. In one embodiment, $R^2$ is H or $O-C_{1-4}$ alkyl. In another embodiment, $R^2$ is H.

$R^4$ is halogen, $OC_{1-4}$ alkyl, $OC_{2-4}$ alkenyl, $OC_{2-4}$ alkynyl, $C_{1-4}$ alkyl, $C_{2-4}$ alkenyl, or $C_{2-4}$ alkynyl. In one embodiment, $R^4$ is halogen or $C_{1-2}$ alkyl. In a further embodiment, $R^4$ is Cl, F, or $C_{1-2}$ alkyl. In still a further embodiment, $R^4$ is Cl, F, or $CH_3$. In another embodiment, $R^4$ is Cl or $CH_3$. In yet another embodiment, $R^4$ is $CH_3$.

$R^5$ is hydrogen, $OC_{1-4}$ alkyl, $OC_{2-4}$ alkenyl, $OC_{2-4}$ alkynyl, OH, $C_{1-4}$ alkyl, $C_{2-4}$ alkenyl, or $C_{2-4}$ alkynyl, each $C_{1-4}$ alkyl, $C_{2-4}$ alkenyl, or $C_{2-4}$ alkynyl independently optionally substituted with 1 to 3 halogens, such as F. In one embodiment, $R^5$ is H, $C_{1-2}$ alkyl, or $OC_{1-2}$ alkyl. In a further embodiment, $R^5$ is $C_{1-2}$ alkyl or $OC_{1-2}$ alkyl. In still a further embodiment, $R^5$ is $CH_3$ or $OCH_3$. In yet a further embodiment, $R^5$ is $CH_3$.

$R^6$ is H, OH, halogen, or $NH_2$. In one embodiment, $R^6$ is H or OH. In a further embodiment, $R^6$ is H.

$R^7$ is H, halogen, OH, $C_{1-4}$ alkyl, $C_{2-4}$ alkenyl, $C_{2-4}$ alkynyl, $OC_{1-4}$ alkyl, $OC_{2-4}$ alkenyl, or $OC_{2-4}$ alkynyl. In one embodiment, $R^7$ is H, $CH_3$, or $OCH_3$. In a further embodiment, $R^7$ is H or $OCH_3$. In another embodiment, $R^7$ is H.

In a particular embodiment of the invention, the compounds of the invention are compounds of Formula II, enantiomers or pharmaceutically acceptable salts thereof:

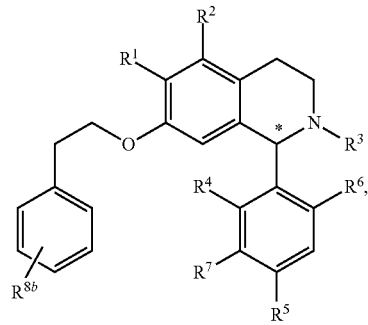

Formula II wherein $R^1$, $R^2$, $R^3$, $R^4$, $R^5$, $R^6$, and $R^7$ are as defined above, and wherein the phenyl ring is substituted with $R^{8b}$ at least once, each $R^{8b}$ independently selected from the group consisting of OH, $C_{1-4}$ alkyl, $OC_{1-4}$ alkyl, $CO_2-C_{1-4}$ alkyl, halogen, $CONH_2$, CN, and COOH. In another embodiment, each $R^{8b}$ is independently selected from the group consisting of OH, $OCH_3$, $CO_2CH_3$, halogen, $CONH_2$, CN, and COOH. In a further embodiment, each $R^{8b}$ is independently selected from the group consisting of OH, $OCH_3$, $CO_2CH_3$, F, $CONH_2$, CN, and COOH. In still another embodiment, each $R^{8b}$ is independently selected from the group consisting of OH, $OCH_3$, and F. In yet a further embodiment, each $R^{8b}$ is independently selected from the group consisting of OH and F. In yet another embodiment, $R^{8b}$ is an OH group. In a further embodiment, at least one $R^{8b}$ substituent is in the meta position relative to the ethyl-oxy group to which the phenyl group is bound.

In a further embodiment of the invention, the compounds of the invention are compounds of Formula IIa, enantiomers or pharmaceutically acceptable salts thereof:

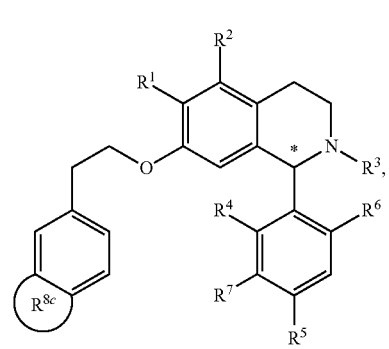

Formula IIa wherein $R^1$, $R^2$, $R^3$, $R^4$, $R^5$, $R^6$, and $R^7$ are as defined above, and wherein $R^{8c}$ is an additional optionally substituted cyclic, heterocyclic, aromatic, or heteroaromatic ring. In one embodiment, $R^{8c}$ is an optionally substituted cyclic, heterocyclic, or heteroaromatic ring.

In a further particular embodiment of the invention, the compounds of the invention are compounds of Formula III, enantiomers or pharmaceutically acceptable salts thereof:

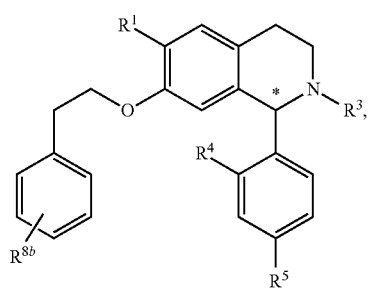

Formula III wherein $R^1$, $R^3$, $R^4$, $R^5$, and $R^{8b}$ are as defined above. In a further embodiment, at least one $R^{8b}$ substituent is in the meta position relative to the ethyl-oxy group to which the phenyl group is bound.

In a preferred embodiment, the compound of the invention is selected from the group consisting of compounds 1-63, enantiomers, and pharmaceutically acceptable salts thereof:

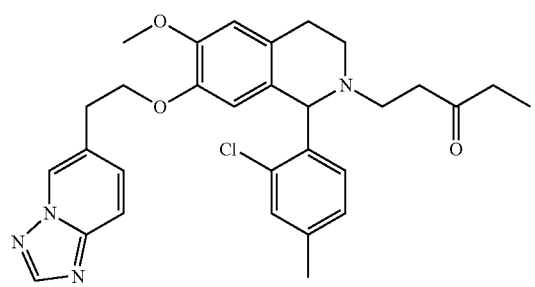

1

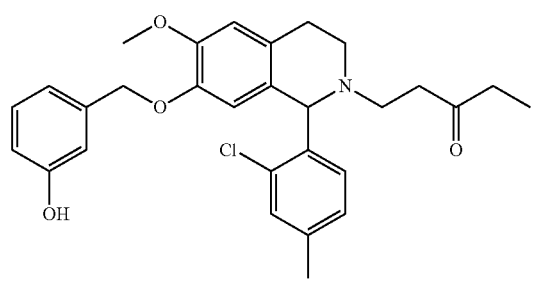

2

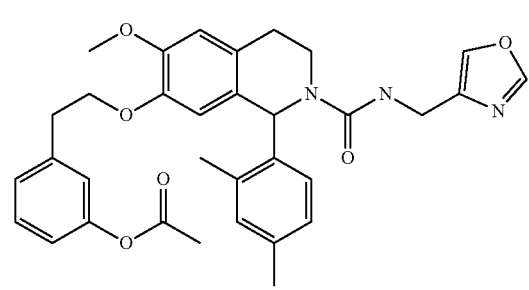

3

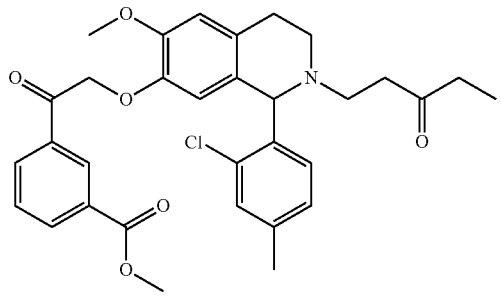

4

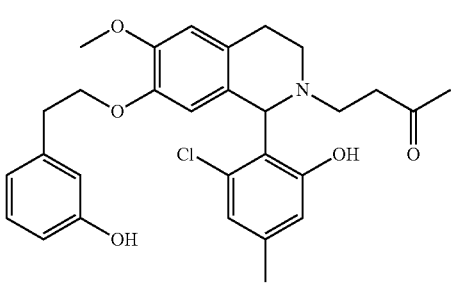

5

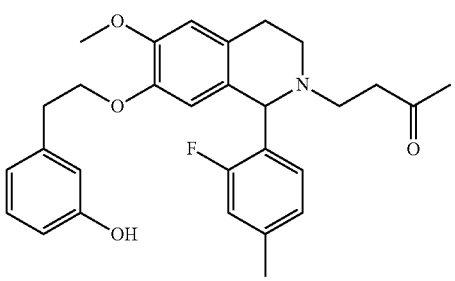

6

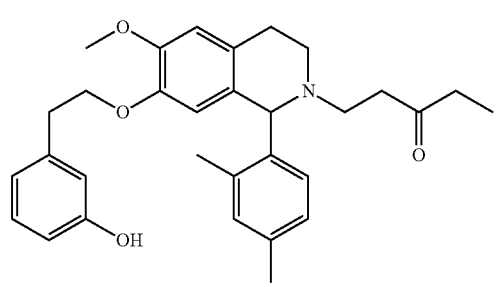

7

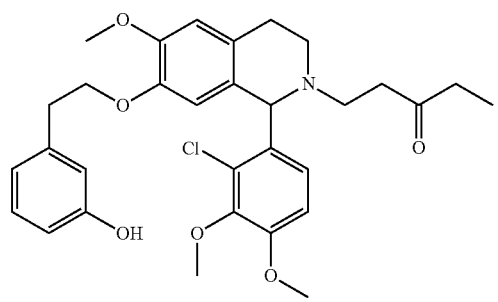

8

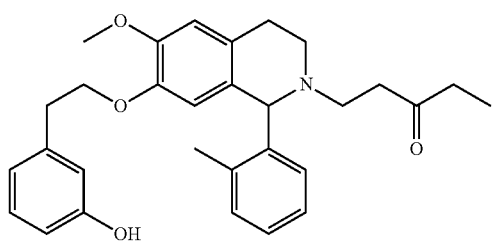
9
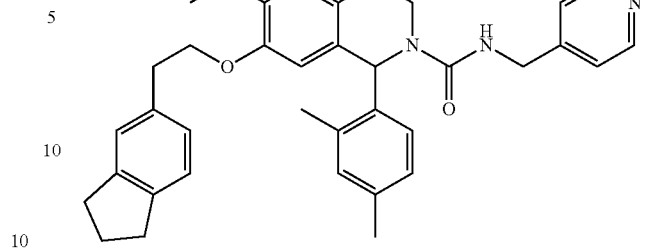
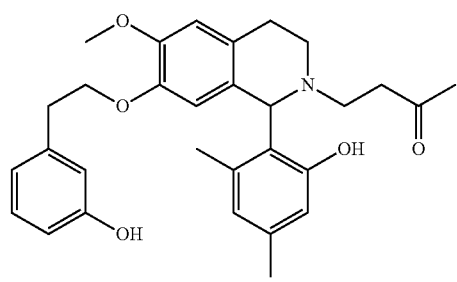
10
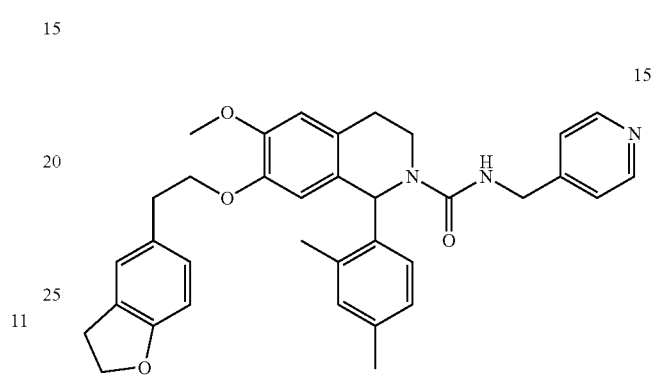
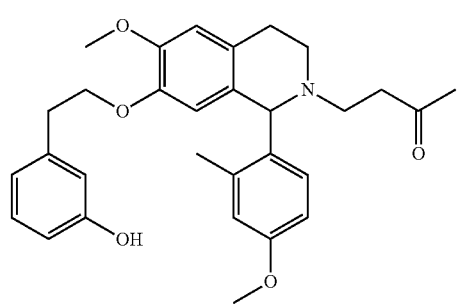
11
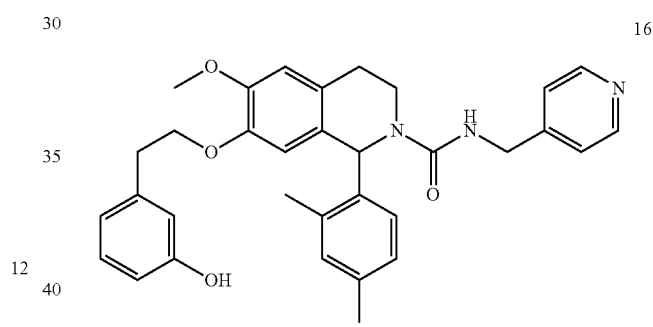
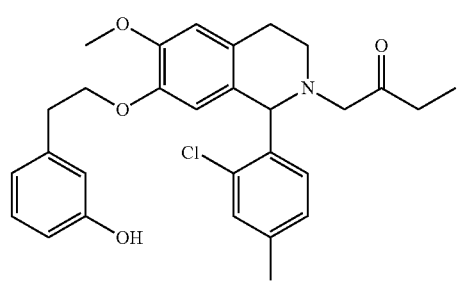
12
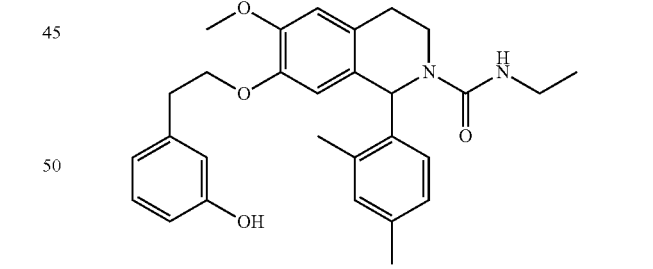
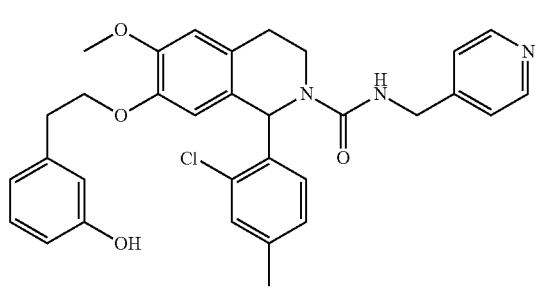
13
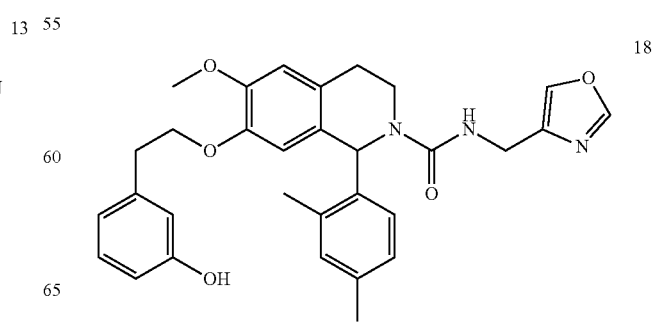
14
15
16
17
18

19
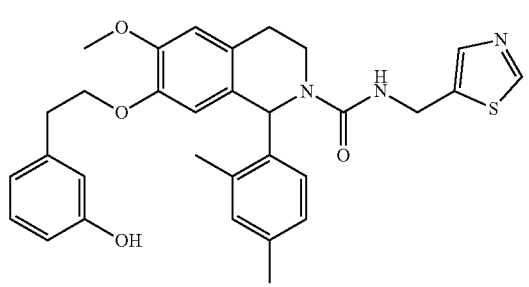
20
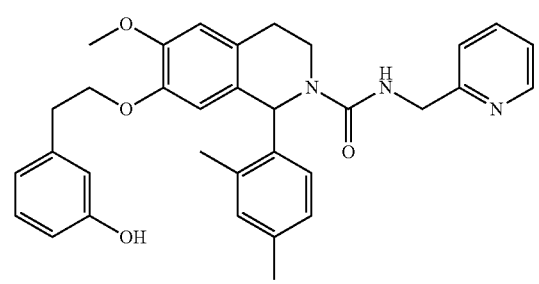
21
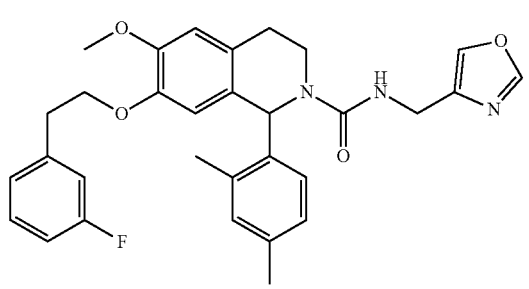
22
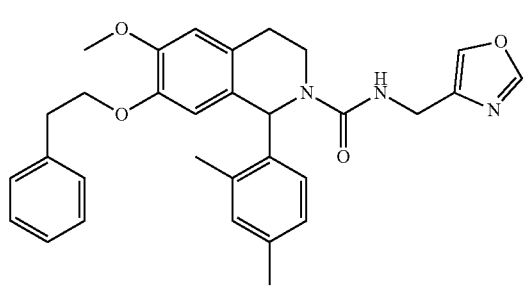
23
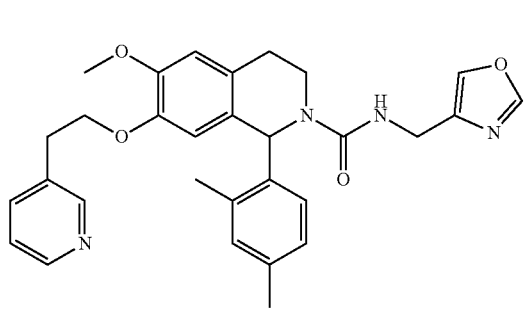
24
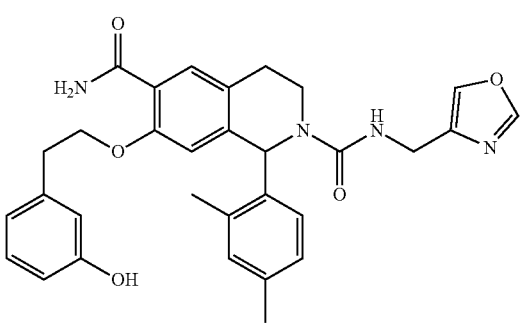
25
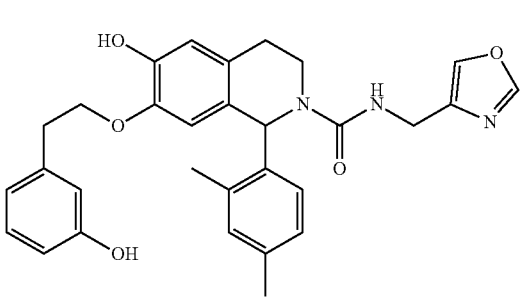
26
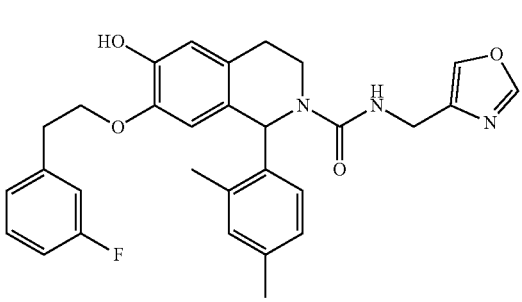
27
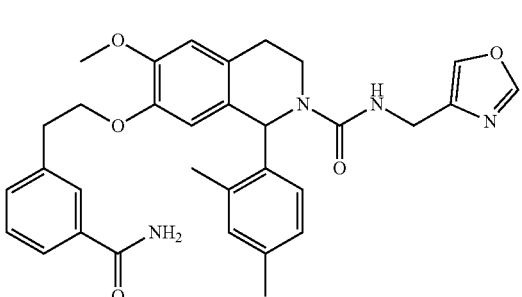
28
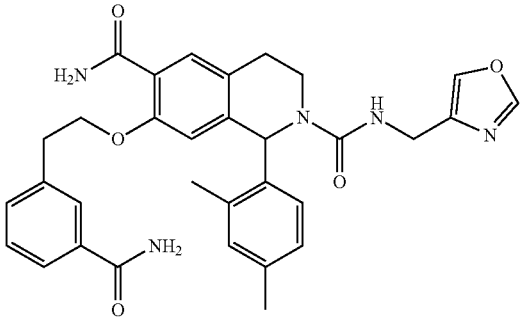

29
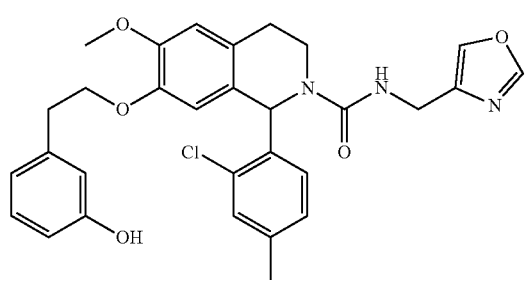
30
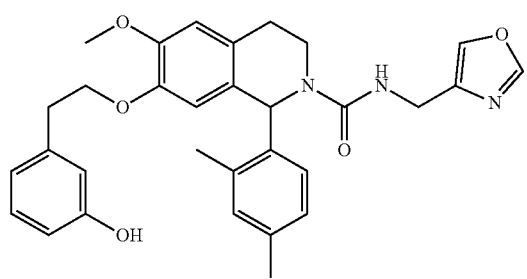
31
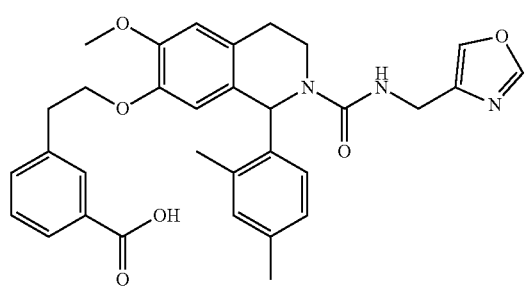
32
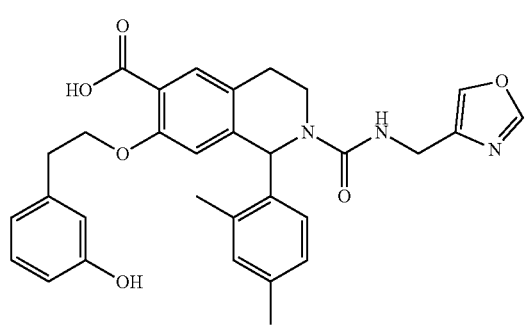
33
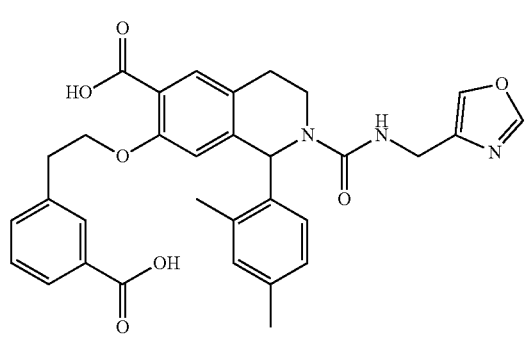
34
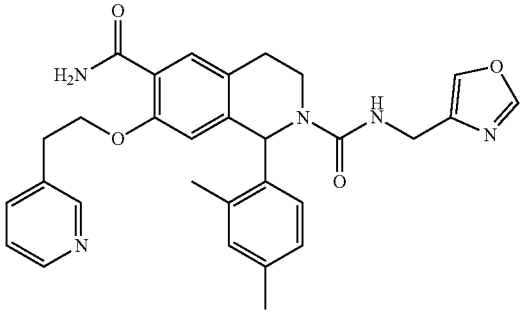
35
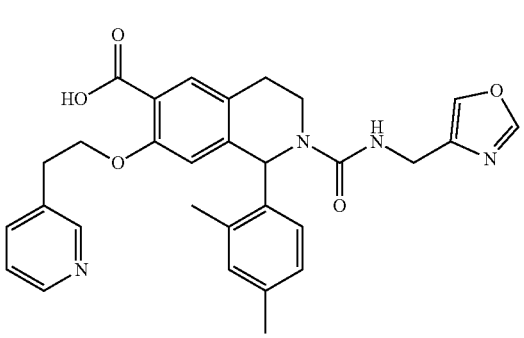
36
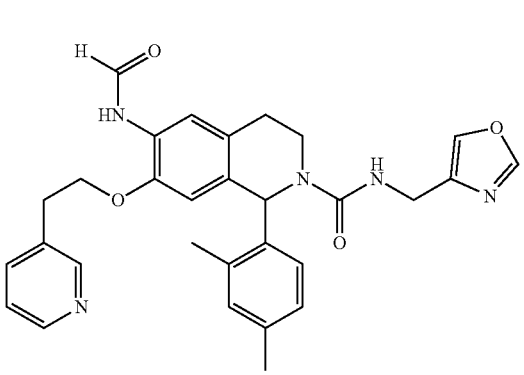
37
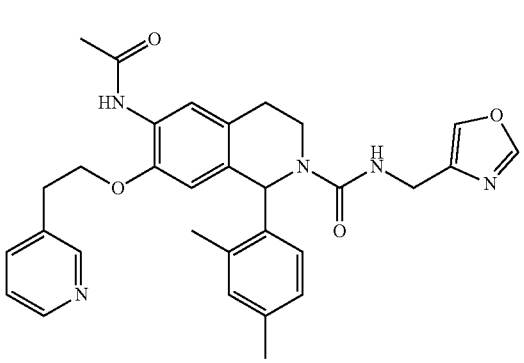
38
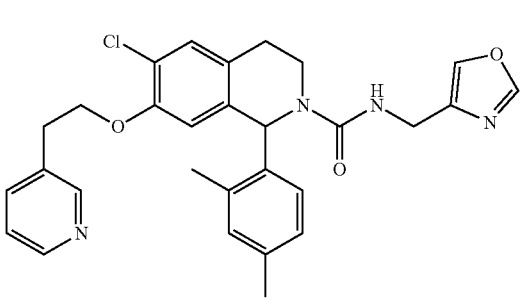

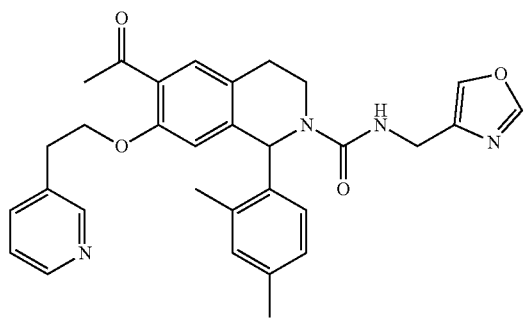
39
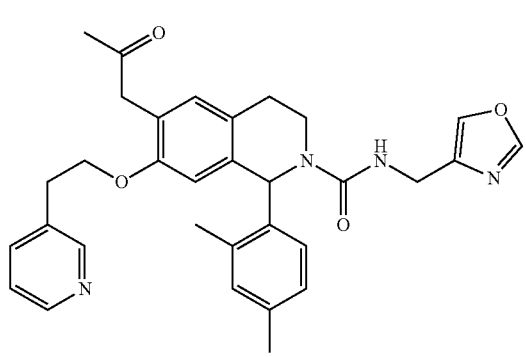
40
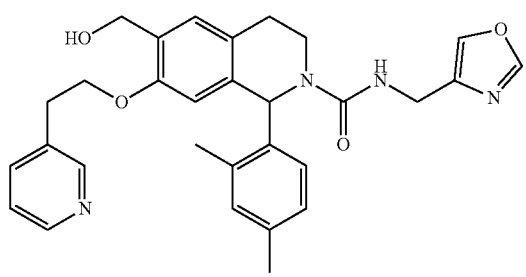
41
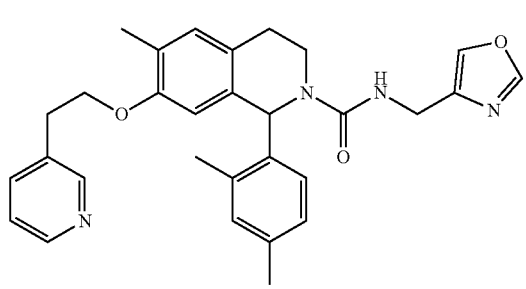
42
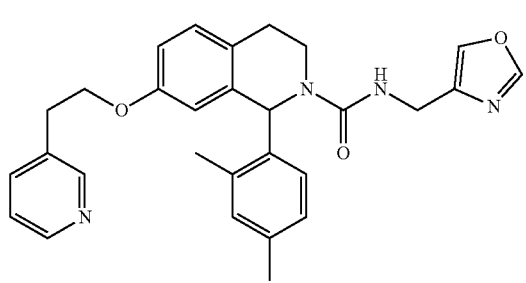
43
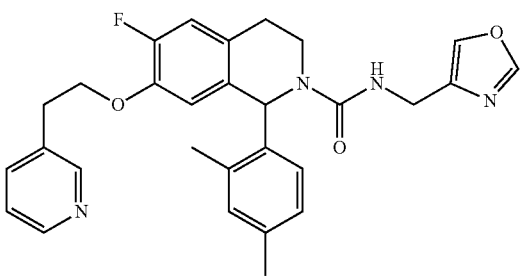
44
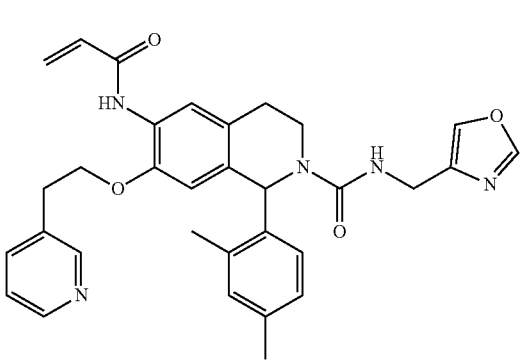
45
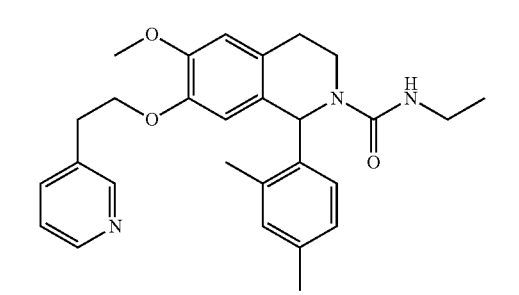
46
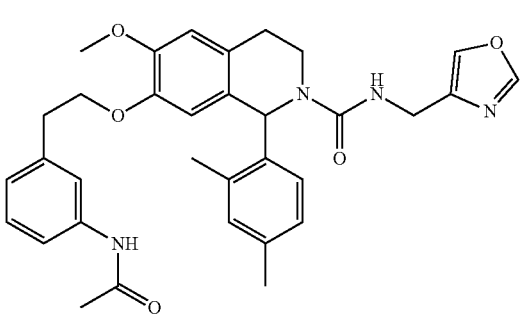
47
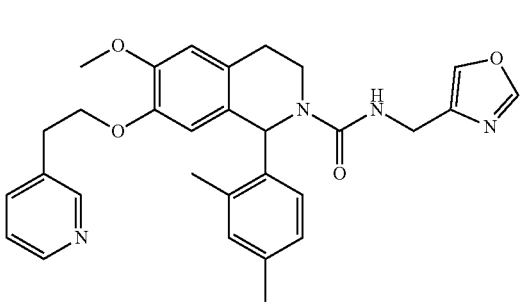
48

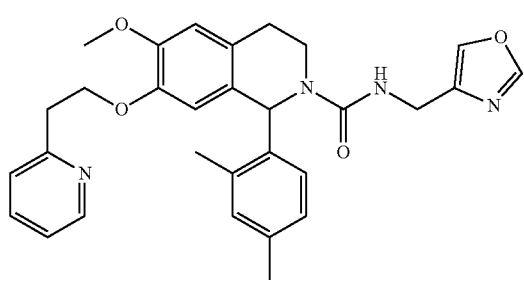
49
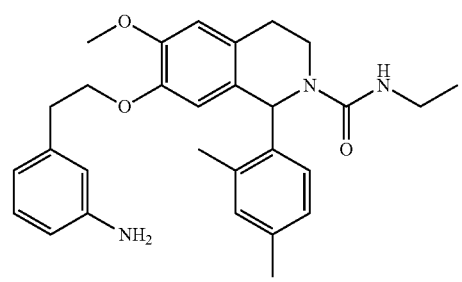
50
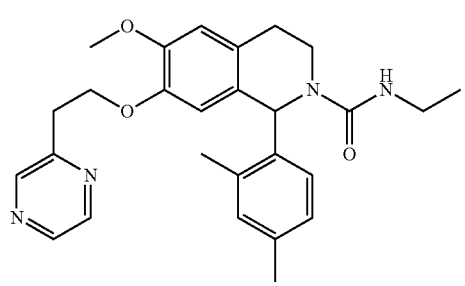
51
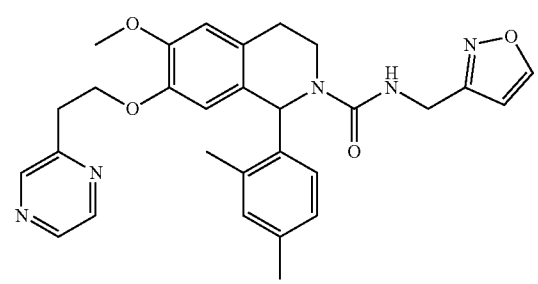
52
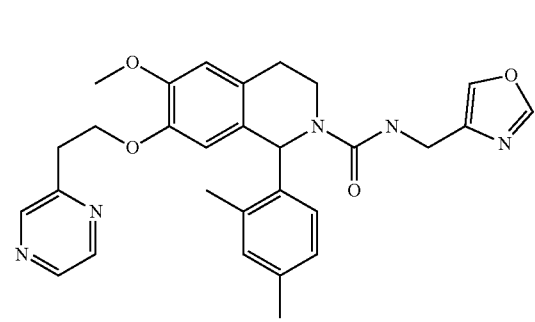
53
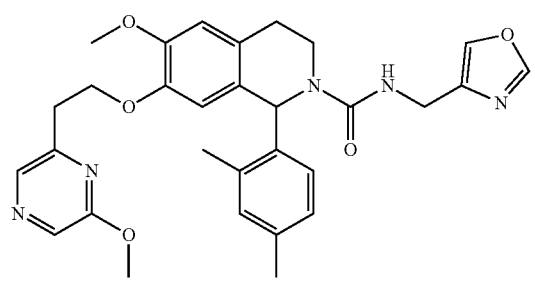
54
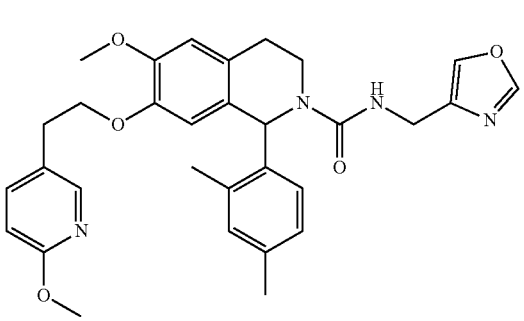
55
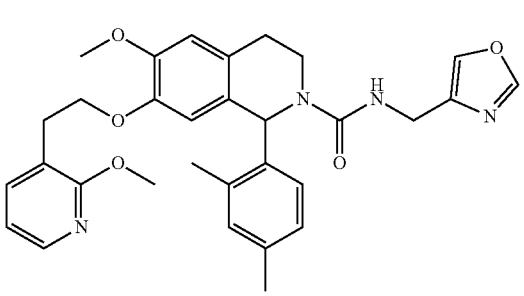
56
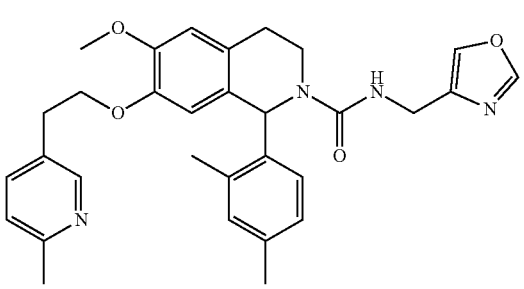
57
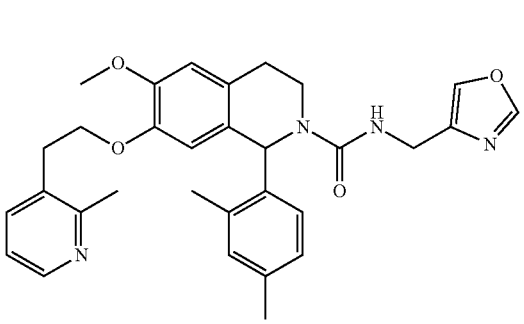
58

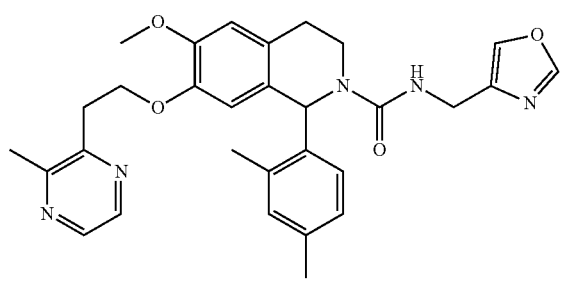

59

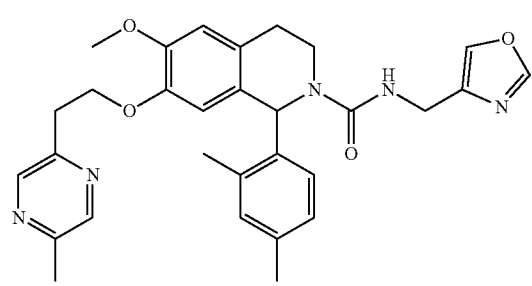

60

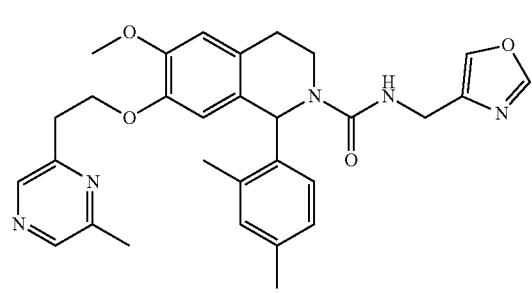

61

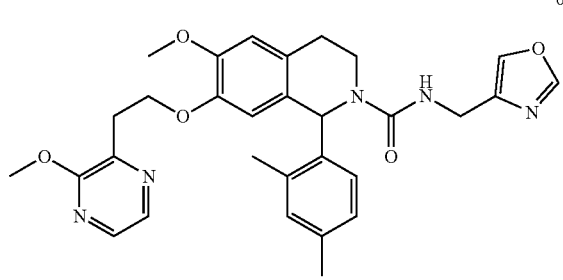

62

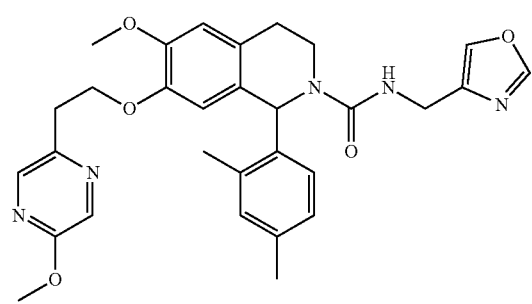

63

Pharmaceutical Formulation

The compounds of the present invention are intended for use as a medicament. The compounds of the invention may in principle be applied on their own, but they are preferably formulated with a pharmaceutically acceptable carrier. A pharmaceutically acceptable carrier is an inert carrier suitable for each administration method, and can be formulated into conventional pharmaceutical preparation (tablets, granules, capsules, powder, solution, suspension, emulsion, injection, infusion, etc.). As such a carrier there may be mentioned, for example, a binder, an excipient, a lubricant, a disintegrant and the like, which are pharmaceutically acceptable. When they are used as an injection solution or an infusion solution, they can be formulated by using distilled water for injection, physiological saline, an aqueous glucose solution.

The administration method of the compounds of the present invention is not particularly limited, and a usual oral or parenteral administration method (intravenous, intramuscular, subcutaneous, percutaneous, intranasal, transmucosal, enteral, etc.) can be applied.

The dosage of the tetrahydroisoquinoline derivatives or a pharmaceutically acceptable salts thereof of the present invention may optionally be set in a range of an effective amount sufficient for showing a pharmacological effect, in accordance with the potency or characteristics of the compound to be used as an effective ingredient. The dosage may vary depending on administration method, age, body weight or conditions of a patient.

Pharmaceutical Utility

The compounds of the invention are intended for the treatment of cancer. Hence, in one aspect, the invention concerns a compound or composition according to the invention for use in the treatment of cancer. In particular Ras-driven cancer, Ras genes being the first oncogenes identified in human cancer cells. In one embodiment, the invention concerns a compound or composition according to the invention for use in the treatment of leukemias, lymphomas, myelomas, colorectal cancer, pancreatic cancer, breast cancer and lung cancer, among other types of cancer.

Preparation of Compounds

The substituted tetrahydroisoquinolines L of the present invention are generally prepared in eight steps as outlined in Scheme 1.

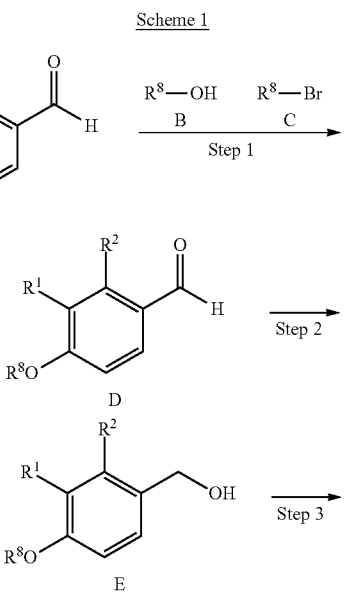

Scheme 1

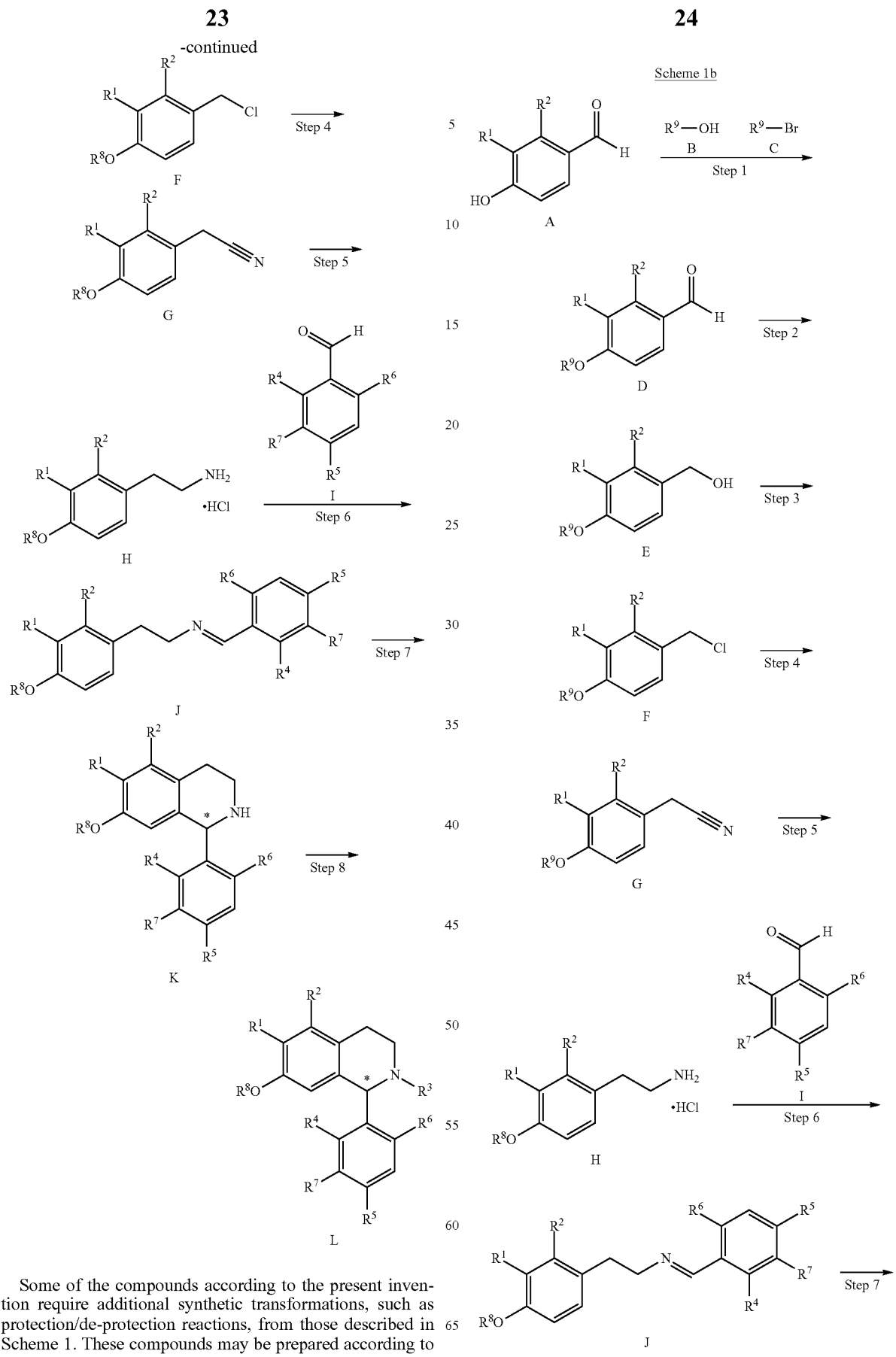
Some of the compounds according to the present invention require additional synthetic transformations, such as protection/de-protection reactions, from those described in Scheme 1. These compounds may be prepared according to Scheme 1b.

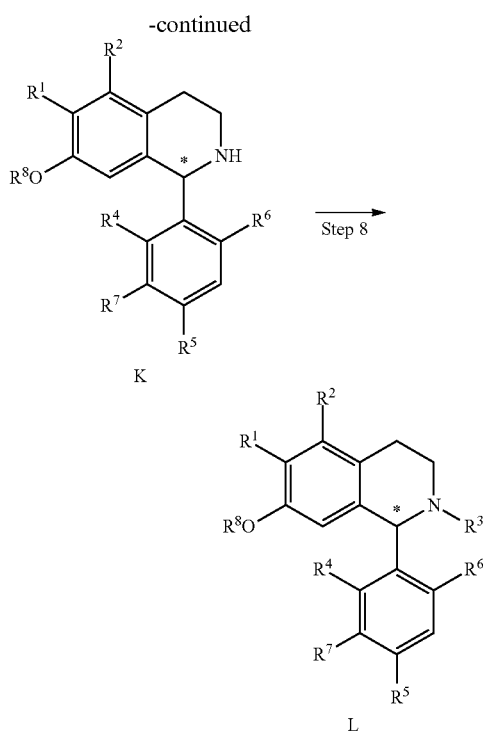

K

L

Scheme 1 and Scheme 1b

At Step 1, ether D is prepared from phenol A by means of a Mitsunobu reaction (reagent B) [G. Liu. et al., *Journal of Medicinal Chemistry* 2007, 50, 3086-3100] or a nucleophilic substitution reaction (reagent C) under suitable conditions well known in the art. $R^9$ is the protected version of $R^8$ in case $R^8$ contains substituents in need of protection during steps 2, 3, and/or 4. One example of $R^9$ could be a benzyloxy-protected $R^8$, where $R^8$ contains a free OH substituent. Reduction of aldehyde D with sodium borohydride in methanol (step 2) leads to alcohol E which is then converted to alkyl chloride F using thionyl chloride (step 3). At step 4, the substitution reaction of compound F using sodium cyanide as the nucleophile provides nitrile G which is reduced to amine H using $H_2$ and 10% Pd/C as the catalyst (step 5). Hydrogenation of nitrile G additionally involves phenol de-protection of those compounds bearing a protecting group in $R^9$ (Scheme 1b) of an OH group in $R^8$. Since hydrochloric acid is used as an additive in the reaction, the amine H is obtained as the hydrochloride salt. Steps 6-7 involve a well-known Pictet-Spengler reaction [A. Yokohama et al., *Journal of Organic Chemistry* 1999, 64, 611-617; R. Gitto et al., *Journal of Medicinal Chemistry* 2003, 46, 197-200] where arylethylamines H are condensed with different substituted benzaldehydes I to give the corresponding imines J which upon treatment with refluxing trifluoroacetic acid undergo intramolecular cyclization to afford tetrahydroisoquinolines K as racemic mixtures. The Bischler-Napieralski reaction [J. E. De Los Angeles. *Journal of Medicinal Chemistry* 1996, 39, 3701-3711; G. Fodor et al., *Angewandte Chemie Int. Ed.* 1972, 11, 919-920] is alternatively used to synthesize tetrahydroisoquinolines K bearing an electron-withdrawing group in the $R^1$ or $R^2$ position. At Step 8, the $R^3$ substituent is introduced by means of different synthetic strategies well known in the art.

Some of the compounds according to the present invention require an alternative synthetic sequence order from that described in the Schemes 1 and 1b. These compounds might be prepared according to Scheme 2 described below.

Scheme 2

At step 1, phenol A is protected using a suitable phenol protecting group $PG^8$, where $PG^8$ may be a benzyl group. Reduction of aldehyde B with sodium borohydride in methanol (step 2) leads to alcohol C which is then converted to alkyl chloride D using thionyl chloride (step 3). At step 4, the substitution reaction of compound D using sodium cyanide as the nucleophile provides nitrile E which is reduced to amine F using $H_2$ and 10% Pd/C as the catalyst (step 5). Since hydrochloric acid is used as an additive in the reaction, the amine F is obtained as a hydrochloride salt. Hydrogenation of nitrile E additionally involves phenol de-protection. Steps 6-7 involve a well-known Pictet-Spengler reaction [A. Yokohama et al., *Journal of Organic Chemistry* 1999, 64, 611-617; R. Gitto et al., *Journal of Medicinal Chemistry* 2003, 46, 197-200] where arylethylamines F are condensed with different substituted benzaldehydes G to give the corresponding imines H which upon treatment with refluxing trifluoroacetic acid undergo intramolecular cyclization to afford tetrahydroisoquinolines I as racemic mixtures. The Bischler-Napieralski reaction [J. E. De Los Angeles. *Journal of Medicinal Chemistry* 1996, 39, 3701-3711; G. Fodor et al., *Angewandte Chemie Int. Ed.* 1972, 11, 919-920] is alternatively used to synthesize tetrahydroisoquinolines I bearing an electron-withdrawing group in the $R^1$ or $R^2$ position. At step 8, amine I is protected using a suitable protecting group $PG^3$, where $PG^3$ may be a Boc protecting group. Phenol alkylation is carried out in step 9 by means of a Mitsunobu reaction (reagent K) [G. Liu. et al., *Journal of Medicinal Chemistry* 2007, 50, 3086-3100] or a nucleophilic substitution (reagent L) under suitable conditions well known in the art. At step 10 the amine group of formula M is de-protected under acidic conditions to provide amine N as a hydrochloride salt. At step 11, the $R^3$ substituent is introduced by means of different synthetic strategies well known in the art.

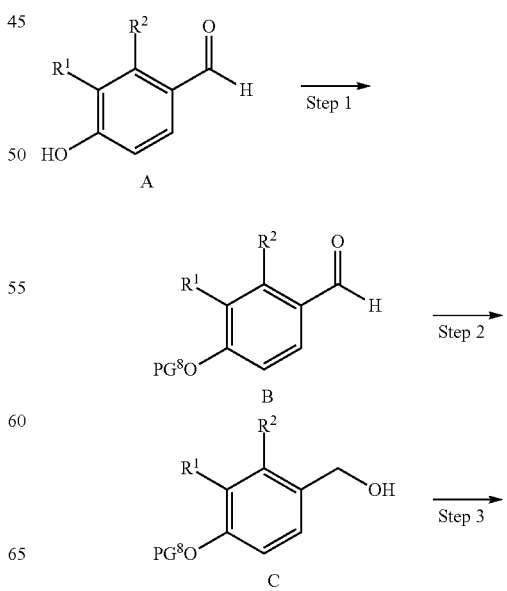

Scheme 2

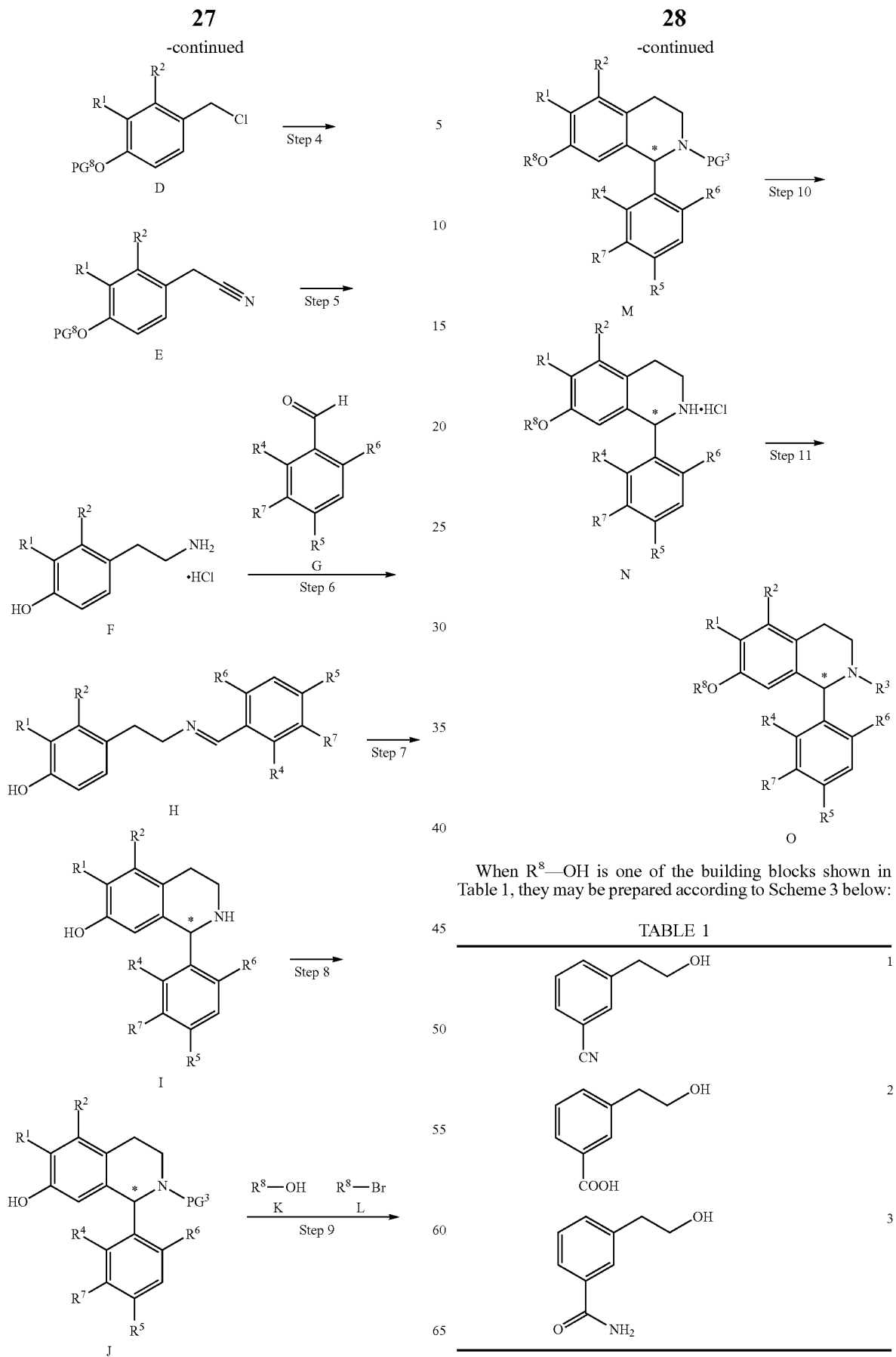
When R⁸—OH is one of the building blocks shown in Table 1, they may be prepared according to Scheme 3 below:
TABLE 1
| | |
|---|---|
| 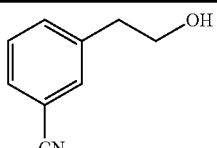 | 1 |
| 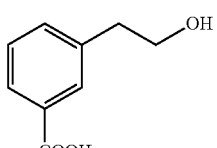 | 2 |
| 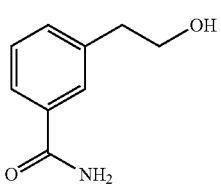 [SMILES: NC(=O)c1cccc(CCO)c1] | 3 |

Scheme 3

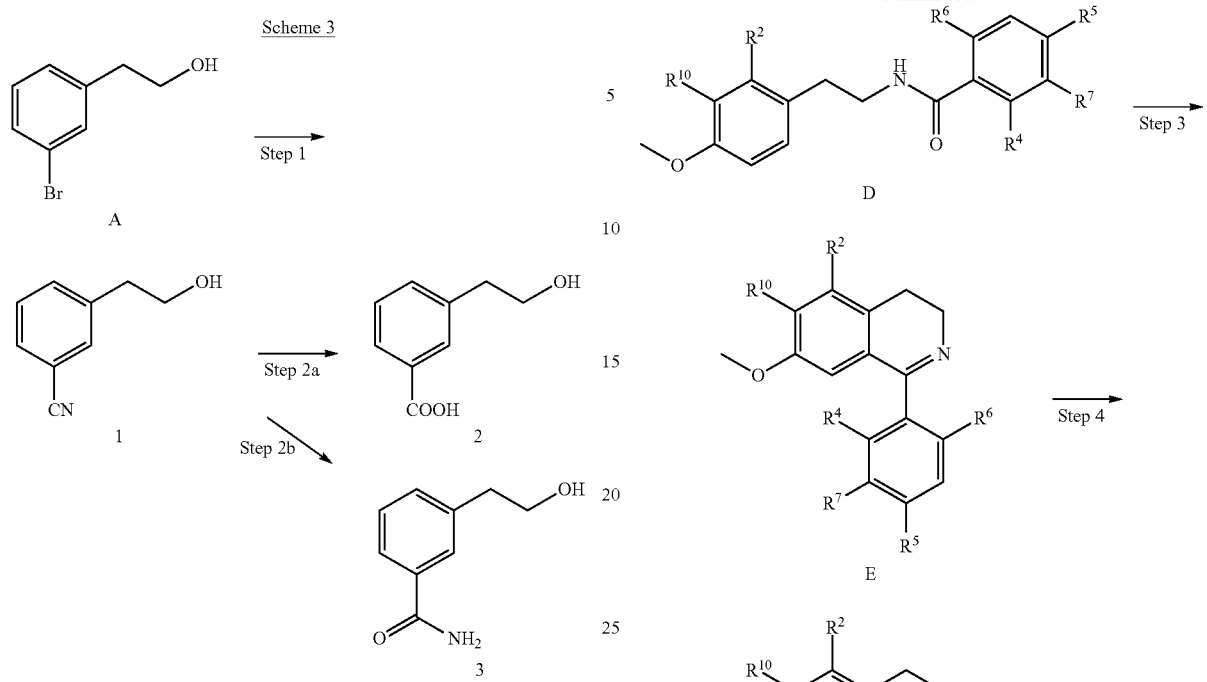

Scheme 3

At step 1, 2-(3-bromophenyl)ethanol A is converted to 3-(2-hydroxyethyl)benzonitrile 1 using copper cyanide [referring to the method disclosed in WO 00/78708 A1, Example 23, pages 28-29]. Compound 1 is then subjected to basic hydrolysis (step 2a) to prepare benzoic acid 2 or to acid hydrolysis (step 2b) to synthesize benzamide 3 [referring to WO 2009/055077 A1, page 384, REAGENT PREPARATION 14].

Some of the compounds according to the present invention require an alternative synthetic procedure from that described in Schemes 1, 1b and 2. These compounds may be prepared according to Scheme 4 below.

Scheme 4

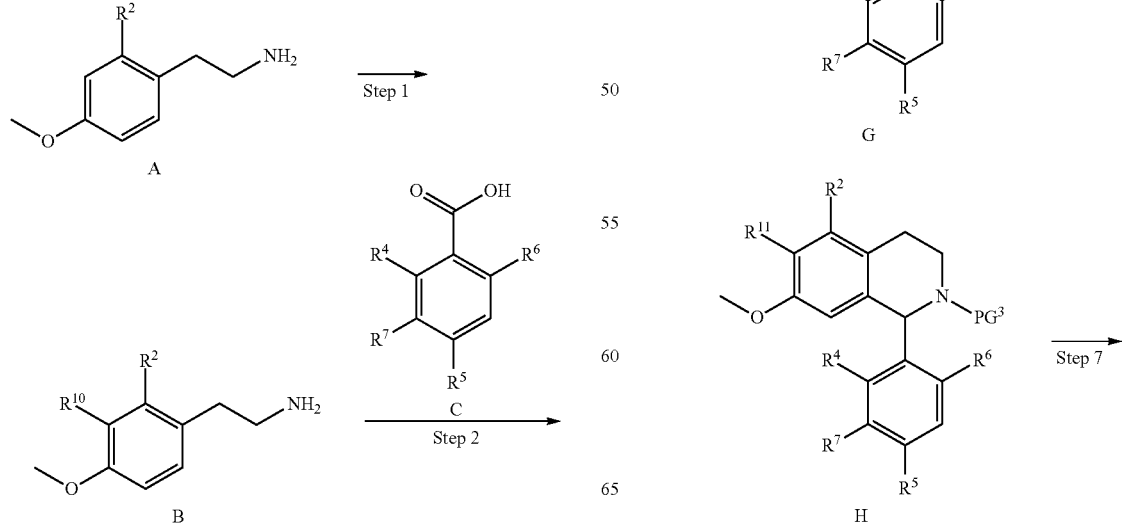

31
-continued
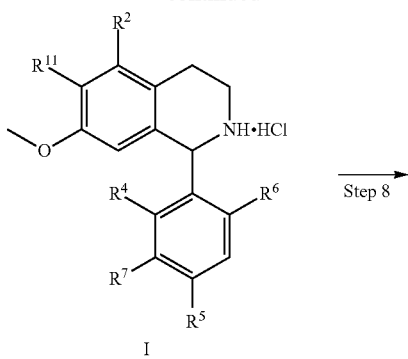
I
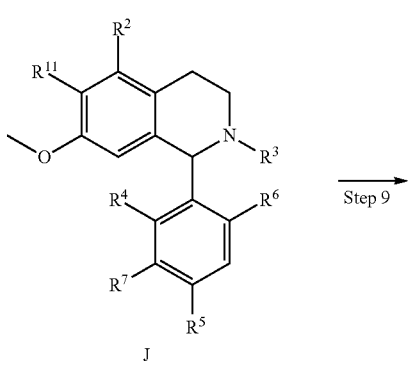
J
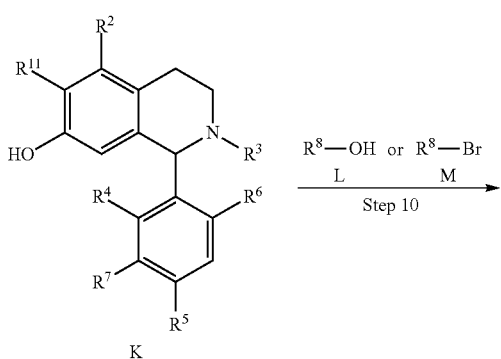
K
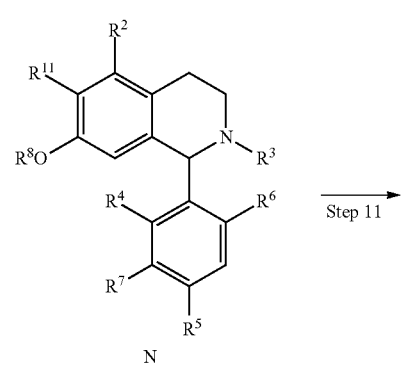
N
32
-continued
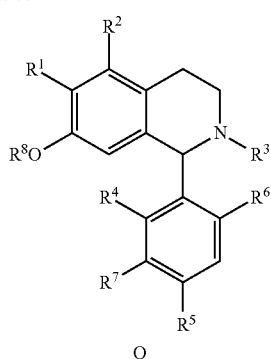
O
Some of the compounds according to the present invention require additional synthetic transformations, such as protection/de-protection reactions, from those described in Scheme 4. These compounds may be prepared according to Scheme 4b.
Scheme 4b
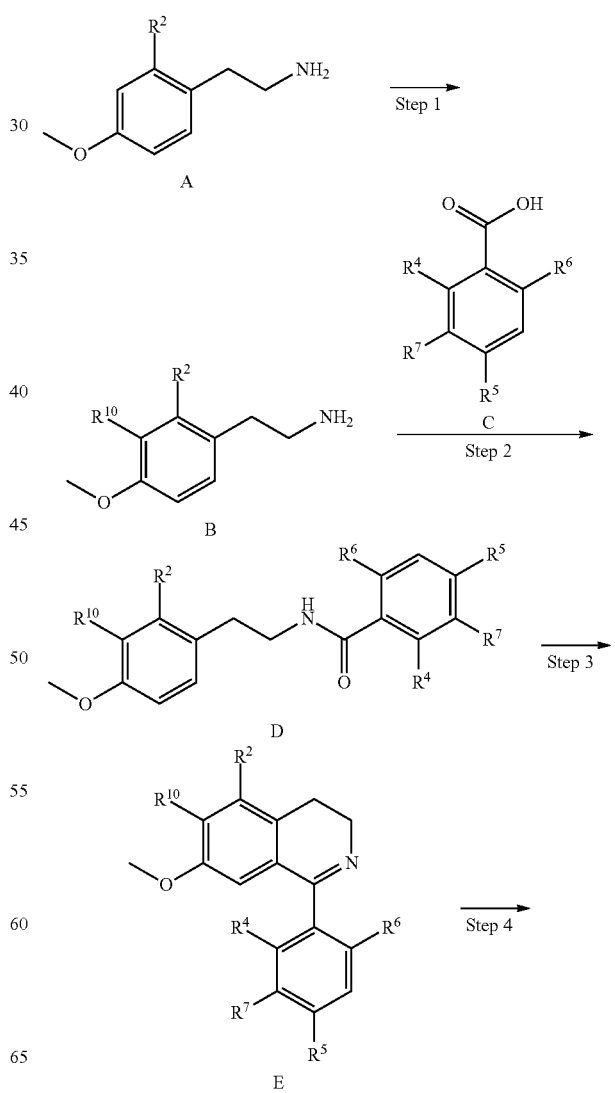

33
-continued
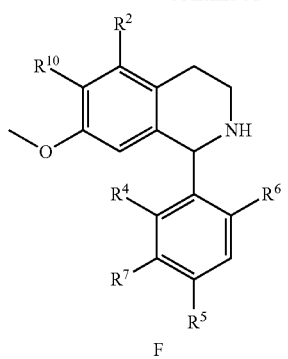
F
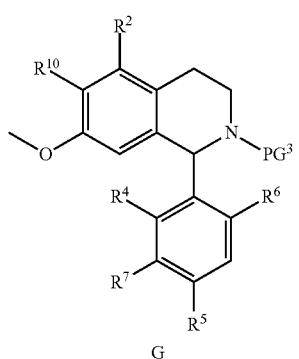
G
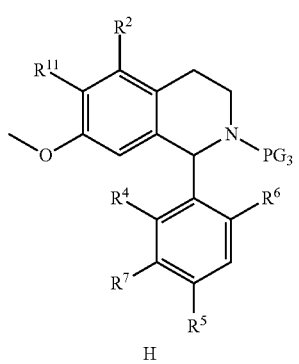
H
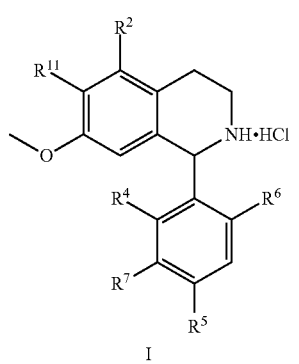
I
Step 5 →
Step 6 →
Step 7 →
Step 8 →
34
-continued
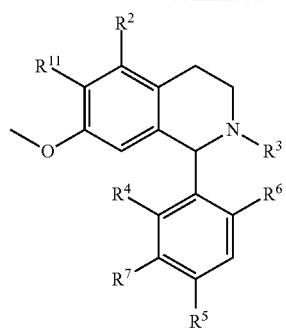
J
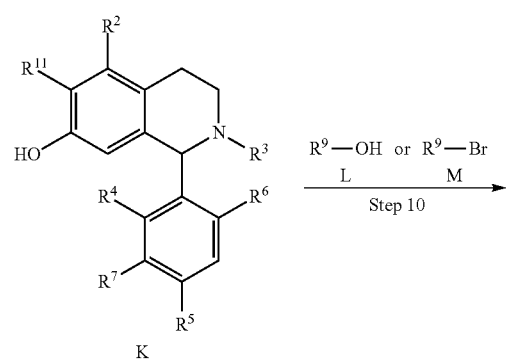
K
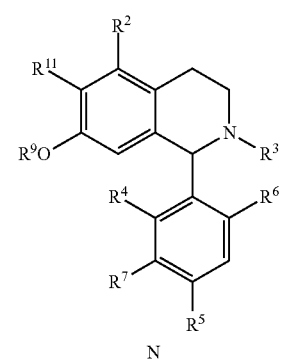
N
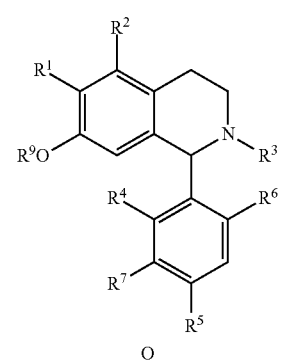
O
Step 9 →
Step 10 →
Step 11 →
Step 12 →

-continued

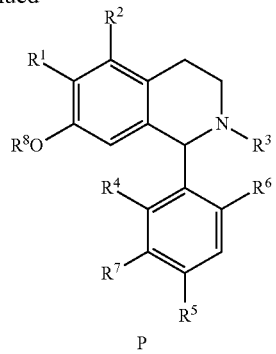

P

Schemes 4 and 4b

At step 1, compound A is subjected to electrophilic aromatic substitution by means of different synthetic strategies well known in the art. At step 2, amine B reacts with acid C under suitable coupling conditions to give amide D. Steps 3-4 involve a well-known Bischler-Napieralski reaction [J. E. De Los Angeles. *Journal of Medicinal Chemistry* 1996, 39, 3701-3711; G. Fodor et al., *Angewandte Chemie Int. Ed.* 1972, 11, 919-920] which is used to synthesize tetrahydroisoquinolines F lacking an electron-donating group in the $R^{10}$ or $R^2$ position. Cyclization of amide D in the presence of phosphorus oxychloride affords dihydroisoquinoline E (step 3) which is subsequently reduced to tetrahydroisoquinoline F at step 4 using sodium borohydride as the reducing agent. Compounds F are obtained as racemic mixtures. At step 5, amine F is protected using a suitable protecting group $PG^3$, where $PG^3$ may be a Boc protecting group. At step 6 the substituent $R^{10}$, which may be a bromine atom, is converted to the corresponding substituent $R^{11}$, which may be a $CH_3OC(O)$— group, by means of different synthetic strategies well known in the art. At step 7 the amine group of formula H is de-protected under acidic conditions to provide amine I as a hydrochloride salt. At step 8 the $R^3$ substituent is introduced by means of different synthetic strategies well known in the art. Step 9 involves reaction of compound J with $BBr_3$ at low temperature to afford compound K [WO 2011/017125, page 110, step 3]. Phenol alkylation is carried out in step 10 by means of a Mitsunobu reaction (reagent L) [G. Liu. et al., *Journal of Medicinal Chemistry* 2007, 50, 3086-3100] or a nucleophilic substitution (reagent M) under suitable conditions well known in the art. At step 11 the substituent $R^{11}$ is converted to the corresponding substituent $R^1$ by means of different synthetic strategies well described in the prior art, which may require different steps depending on the nature of the substituent $R^1$. Hydrogenation of compound O (scheme 4b) involves phenol de-protection of those compounds bearing a protecting group in $R^9$.

When $R^3$ is $C(O)NHR^{3a}$, i.e. when $n^3$ is O, $Y_3$ is O, $X^3$ is NH, $m^3$ is 1, and $k^3$ is 0, amine K (Scheme 1) or amine N (Scheme 2) are coupled with $R^{3a}NH_2$ using 1,1-carbonyldiimidazole as coupling agent and a suitable base (e.g. triethylamine) to afford the corresponding ureas L and O respectively [WO 2015/089337].

When $R^3=C_{1-2}$ alkyl-$C(Y^3)$—$(X^3)_{m}{}^3$—$(CH_2)_k{}^3$—$R^{3a}$, i.e. when $n^3$ is 1 or 2, amine L (Scheme 1) or amine O (Scheme 2) are prepared via nucleophilic substitution using Cl—$C_{1-2}$-alkyl-$C(Y^3)$—$(X^3)_m{}^3$—$(CH_2)_k{}^3$—$R^{3a}$ or Br—$C_{1-2}$-alkyl-$C(Y^3)$—$(X^3)_m{}^3$—$(CH_2)_k{}^3$—$R^{3a}$ and a suitable base (e.g. triethylamine).

EXAMPLES

Example 1—Synthesis of compound 18: 1-(2,4-dimethylphenyl)-7-(3-hydroxyphenethoxy)-6-methoxy-N-(oxazol-4-ylmethyl)-3,4-dihydroisoquinoline-2(1H)-carboxamide Step 1—Synthesis of 2-(3-(benzyloxy)phenyl)ethanol

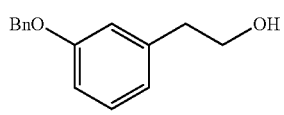 [SMILES: OCCc1cccc(OCc2ccccc2)c1]

To a solution of 2-(3-Hydroxyphenyl)ethanol (2.2 g, 15.6 mmol) in dry dimethylformamide (40 mL) was added potassium carbonate (4.3 g, 31.1 mmol). After stirring for 10 min at room temperature, benzyl bromide (1.9 mL, 15.6 mmol) was added and the reaction was stirred at 50° C. After 2 h, the reaction mixture was partitioned between ethyl acetate and water. The organic layer was washed with brine, dried over anhydrous $MgSO_4$ filtered and concentrated under vacuo to provide the product as a yellow oil (2.7 g, 77% yield). $^1H$ NMR (400 MHz, $CDCl_3$) δ ppm 7.33-7.45 (m, 5H), 7.22-7.26 (m, 1H), 6.83-6.87 (m, 3H), 5.06 (s, 2H), 3.88 (t, J=6.2 Hz, 2H), 2.85 (t, J=6.3 Hz, 2H).

Step 2—Synthesis of 4-(3-(benzyloxy)phenethoxy)-3-methoxybenzaldehyde

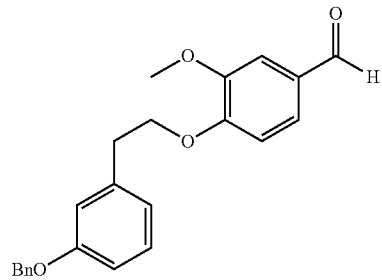 [SMILES: COc1cc(C=O)ccc1OCCc1cccc(OCc2ccccc2)c1]

To a solution of 2-(3-(benzyloxy)phenyl)ethanol (1.5 g, 6.6 mmol) in dry tetrahydrofuran (25 mL), 4-hydroxy-3-methoxybenzaldehyde (1.0 g, 6.6 mmol) and triphenylphosphine (2.3 g, 8.5 mmol) were added, followed by the slow addition of diisopropylazodicarboxylate (1.8 mL, 8.5 mmol). The reaction was stirred at room temperature for 2 h. The solvent was evaporated under vacuo and the residue purified by column chromatography on silica gel (Ethyl Acetate:Hexane=20:80) to give the title compound as a white solid (1.7 g, 72% yield). $^1H$ NMR (400 MHz, $CDCl_3$) δ ppm 9.85 (s, 1H), 7.31-7.45 (m, 7H), 7.23 (d, J=7.9 Hz, 1H), 6.94-6.96 (m, 2H), 6.86-6.90 (m, 2H), 5.06 (s, 2H), 4.28 (t, J=7.4 Hz, 2H), 3.93 (s, 3H), 3.17 (t, J=7.4 Hz, 2H).

Step 3—Synthesis of (4-(3-(benzyloxy)phenethoxy)-3-methoxyphenyl)methanol

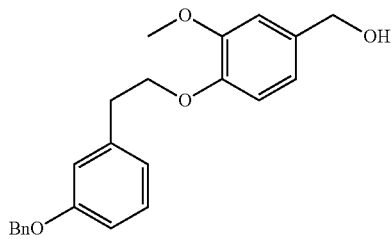

To a solution of 4-(3-(benzyloxy)phenethoxy)-3-methoxybenzaldehyde (1.7 g, 4.7 mmol) in methanol (93 mL), sodium borohydride (0.7 g, 18.9 mmol) was added in portions. The mixture was stirred at room temperature for 1 h. The solvent was evaporated under vacuo and excess reagent remaining in the residue was decomposed with water and extracted with ethyl acetate. The extract was washed with water, dried over anhydrous MgSO$_4$, filtered and concentrated to give the product as a colourless oil (1.6 g, 94% yield). $^1$H NMR (400 MHz, CDCl$_3$) δ ppm 7.30-7.45 (m, 5H), 7.21-7.26 (m, 1H), 6.94-6.96 (m, 2H), 6.83-6.90 (m, 4H), 5.06 (s, 2H), 4.62 (d, J=4.8 Hz, 2H), 4.21 (t, J=7.6 Hz, 2H), 3.88 (s, 3H), 3.13 (t, J=7.5 Hz, 2H).

Step 4—Synthesis of 1-(3-(benzyloxy)phenethoxy)-4-(chloromethyl)-2-methoxybenzene

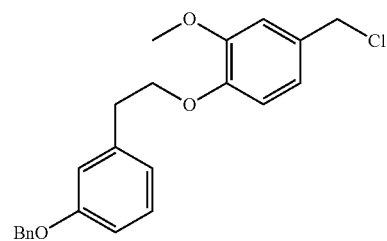

To a solution of (4-(3-(benzyloxy)phenethoxy)-3-methoxyphenyl)methanol (1.6 g, 4.4 mmol) in dry toluene (24 mL), thionyl chloride (0.43 mL, 5.8 mmol) was added dropwise. The mixture was stirred for 45 minutes at room temperature and then refluxed for 1.5 hours. The solvent was evaporated to give the compound as a viscous oil, which was used immediately without purification.

Step 5—Synthesis of 2-(4-(3-(benzyloxy)phenethoxy)-3-methoxyphenyl)acetonitrile

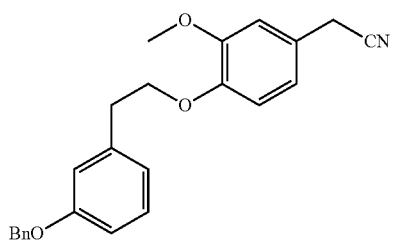 [SMILES: COc1cc(CO)ccc1OCCc1cccc(OCc2ccccc2)c1]

To a solution of 1-(3-(benzyloxy)phenethoxy)-4-(chloromethyl)-2-methoxybenzene (1.7 g, 4.4 mmol) in acetonitrile (72 mL) was added sodium cyanide (0.9 g, 17.8 mmol) and sodium iodide (0.9 g, 6.2 mmol). The reaction was stirred at reflux. After 2 h, the reaction mixture was partitioned between ethyl acetate and water. The extract was dried over anhydrous MgSO$_4$, filtered and the solvent evaporated under vacuo. The residue was purified by column chromatography on silica gel (Ethyl acetate:Hexane=20:80) to give the title compound as a yellow oil (1.2 g, 72% yield). $^1$H NMR (400 MHz, CDCl$_3$) δ ppm 7.31-7.45 (m, 5H), 7.21-7.25 (m, 1H), 6.94-6.95 (m, 1H), 6.85-6.89 (m, 2H), 6.83 (s, 3H), 5.06 (s, 2H), 4.20 (t, J=7.5 Hz, 2H), 3.87 (s, 3H), 3.69 (s, 2H), 3.13 (t, J=7.5 Hz, 2H).

Step 6—Synthesis of 3-(2-(4-(2-aminoethyl)-2-methoxyphenoxy)ethyl)phenol hydrochloride

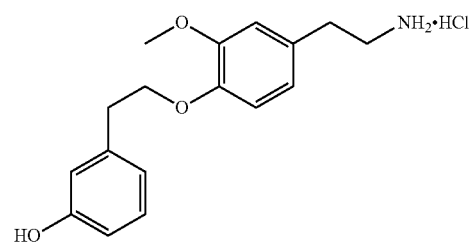

A solution of 2-(4-(3-(benzyloxy)phenethoxy)-3-methoxyphenyl)acetonitrile (1.2 g, 3.2 mmol) in tetrahydrofuran (12 mL), methanol (35 mL) and concentrated HCl (0.63 mL) was shaken under hydrogen atmosphere (1.5 Atm) at room temperature in the presence of 10% Pd on charcoal (0.24 g, 20% weight). After 24 h the product was isolated by filtering off the catalyst and washing with methanol. The filtrate was evaporated under reduced pressure to give the product as a beige solid (1.0 g, 97% yield). $^1$H NMR (400 MHz, CD$_3$OD) δ ppm 7.09 (t, J=7.8 Hz, 1H), 6.89-6.92 (m, 2H), 6.73-6.80 (m, 3H), 6.63 (dd, J=8.1, 1.8 Hz, 1H), 4.16 (t, J=7.0 Hz, 2H), 3.83 (s, 3H), 3.15 (t, J=7.6 Hz, 2H), 2.99 (t, J=7.0 Hz, 2H), 2.89 (t, J=7.6 Hz, 2H).

Step 7—Synthesis of 3-(2-((1-(2,4-dimethylphenyl)-6-methoxy-1,2,3,4-tetrahydroisoquinolin-7-yl)oxy)ethyl)phenol 2,2,2-trifluoroacetate

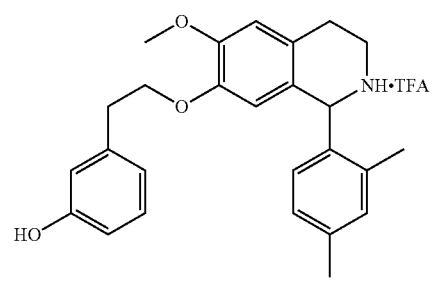

Step 7A. 3-(2-(4-(2-((2,4-dimethylbenzylidene)amino)ethyl)-2-methoxyphenoxy)ethyl)phenol

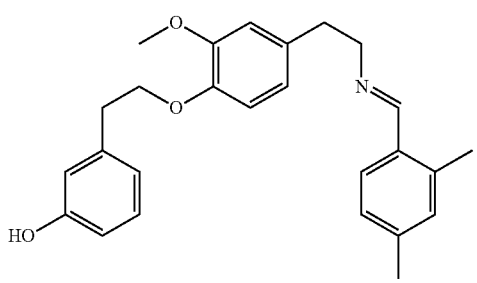 [SMILES: COc1cc(CC/N=C/c2ccc(C)cc2C)ccc1OCCc1cccc(O)c1]

To a solution of 3-(2-(4-(2-aminoethyl)-2-methoxyphenoxy)ethyl)phenol hydrochloride (0.78 g, 2.4 mmol) in methanol (9 mL), triethylamine (2.6 mL, 18.9 mmol) and activated molecular sieves were added followed by the addition of 2,4-dimethylbenzaldehyde (0.35 g, 2.4 mmol) in toluene (15 mL). The reaction was stirred at reflux. After 2 h, the reaction mixture was dried over anhydrous MgSO$_4$, diluted with dichloromethane, filtered and concentrated under vacuo to give the crude product which was immediately used as starting material in step B.

Step 7B. 3-(2-((1-(2,4-dimethylphenyl)-6-methoxy-1,2,3,4-tetrahydroisoquinolin-7-yl)oxy)ethyl)phenol 2,2,2-trifluoroacetate

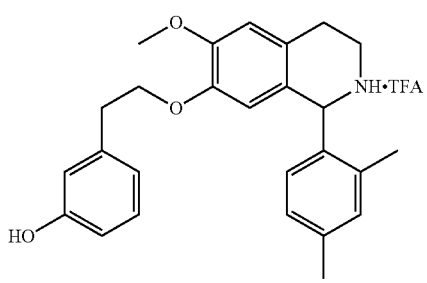

3-(2-(4-(2-((2,4-dimethylbenzylidene)amino)ethyl)-2-methoxyphenoxy)ethyl)phenol was mixed with trifluoroacetic acid (25 mL). The reaction was stirred at reflux for 3 h. The reaction mixture was diluted with water and extracted with dichloromethane (×3). The combined organic layers were dried over anhydrous MgSO$_4$, filtered and concentrated under vacuo. The residue was purified by reverse phase chromatography (acetonitrile+0.1% TFA/water+0.1% TFA 0-100% gradient) to give the title product as a beige solid (0.48 g, 39% yield). $^1$H NMR (400 MHz, CD$_3$OD) δ ppm 7.22 (s, 1H), 7.08 (d, J=7.7 Hz, 1H), 7.02 (t, J=7.9 Hz, 1H), 6.92 (d, J=7.9 Hz, 1H), 6.88 (s, 1H), 6.54-6.61 (m, 3H), 6.20 (s, 1H), 5.84 (s, 1H), 3.93-3.98 (m, 1H), 3.86-3.90 (m, 1H), 3.84 (s, 3H), 3.47-3.58 (m, 2H), 3.20-3.28 (m, 1H), 3.06-3.13 (m, 1H), 2.80-2.83 (m, 2H), 2.48 (s, 3H), 2.34 (s, 3H).

Step 8—Synthesis of 1-(2,4-dimethylphenyl)-7-(3-hydroxyphenethoxy)-6-methoxy-N-(oxazol-4-ylmethyl)-3,4-dihydroisoquinoline-2(1H)-carboxamide

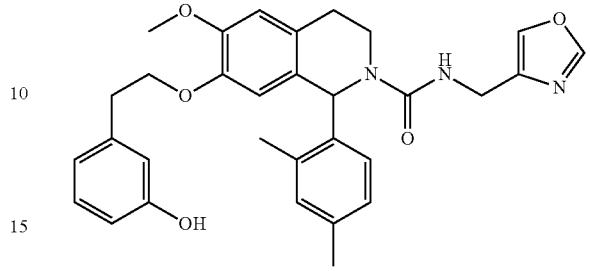

To a suspension of oxazol-4-ylmethanamine dihydrochloride (0.08 g, 0.46 mmol) in dry dimethylformamide (0.3 mL) was added triethylamine (0.13 mL). The mixture was stirred at room temperature for 10 min, after which time was added carbonyldiimidazole (0.04 g, 0.23 mmol). The mixture was stirred at room temperature for 1 h, after which time was added 3-(2-((1-(2,4-dimethylphenyl)-6-methoxy-1,2,3,4-tetrahydroisoquinolin-7-yl)oxy)ethyl)phenol 2,2,2-trifluoroacetate (0.06 g, 0.12 mmol) dissolved in dry dimethylformamide (0.7 mL). The reaction was stirred at room temperature. After 4 h, the reaction mixture was partitioned between ethyl acetate and water. The organic layer was washed with brine, dried over anhydrous MgSO$_4$, filtered and concentrated under vacuo. The residue was purified by reverse phase chromatography (acetonitrile/water 0-100% gradient) to give the title product as a white solid (0.028 g, 46% yield). $^1$H NMR (400 MHz, CDCl$_3$) δ ppm 7.83 (s, 1H), 7.56 (s, 1H), 7.08 (t, J=7.8 Hz, 1H), 7.00 (s, 1H), 6.82 (d, J=7.7 Hz, 1H), 6.56-6.71 (m, 5H), 6.35 (s, 1H), 6.29 (s, 1H), 6.11 (bs, 1H), 5.20 (t, J=5.5 Hz, 1H), 4.37 (d, J=5.4 Hz, 2H), 4.07 (t, J=7.2 Hz, 2H), 3.84 (s, 3H), 3.60 (dd, J=14.4, 5.6 Hz, 1H), 3.29 (ddd, J=14.5, 12.4, 4.3 Hz, 1H), 2.91-3.01 (m, 3H), 2.61 (dd, J=16.4, 2.9 Hz, 1H), 2.40 (s, 3H), 2.26 (s, 3H).

In addition to compound 18, compounds 3, 5-13, 16, 17, 19-22, 25, 26, 29, and 46-53 may also be prepared according to schemes 1 or 1b. Compounds 1, 2, 4, 14, 15, 23 and 54-63 may be prepared according to scheme 2. Compounds 27, 30 and 31 may be prepared according to schemes 2 and 3.

Example 2—Synthesis of compound 34: 1-(2,4-dimethylphenyl)-N2-(oxazol-4-ylmethyl)-7-(2-(pyridin-3-yl)ethoxy)-3,4-dihydroisoquinoline-2,6(1H)-dicarboxamide

Step 1—Synthesis of 2-(3-bromo-4-methoxyphenyl)ethanamine

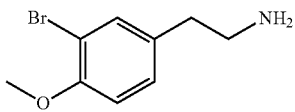

A solution of bromine (1.54 mL, 30 mmol) in dichloromethane (40 mL) was added dropwise to a stirred solution of 2-(4-methoxyphenyl)ethanamine (2.27 g, 15 mmol) in acetic acid (48 mL). After 2 h, the reaction mixture was concentrated under vacuo and the residue purified by reverse phase chromatography (acetonitrile/water 0-100% gradient) to afford the title product (920 mg, 40% yield). ¹H NMR (400 MHz, CDCl₃) δ ppm 7.33 (d, J=1.5 Hz, 1H), 7.13 (d, J=7.5 Hz, 1H), 7.12 (dd, J=7.5, 1.5 Hz, 1H), 5.11 (bs, 2H), 3.83 (s, 3H), 2.98 (t, J=7.1 Hz, 2H), 2.83 (t, J=7.1 Hz, 2H).

Step 2—Synthesis of N-(3-bromo-4-methoxyphenethyl)-2,4-dimethylbenzamide

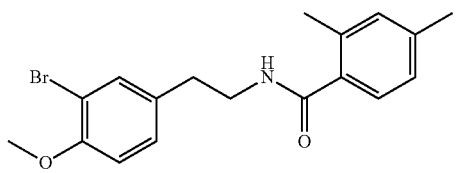

1-Ethyl-3-(3-dimethylaminopropyl)carbodiimide hydrochloride (226 mg, 1.18 mmol) and N,N-diisopropylethylamine (1.03 mL, 5.90 mmol) were added to a solution of 2-(3-bromo-4-methoxyphenyl)ethanamine (226 mg, 0.98 mmol), 2,4-dimethylbenzoic acid (151 mg, 0.98 mmol) and 1-hydroxybenzotriazole hydrate (160 mg, 1.18 mmol) in dry N,N-dimethylformamide. After 24 h the reaction mixture was partitioned between ethyl acetate and water. The organic layer was dried over anhydrous MgSO₄, filtered and concentrated under vacuo. The residue was purified by reverse phase chromatography (acetonitrile/water 0-100% gradient) to give the title product as a pale yellow solid (0.32 g, 90% yield). ¹H NMR (400 MHz, CDCl₃) δ ppm 7.43 (d, J=2.1 Hz, 1H), 7.12-7.20 (m, 2H), 6.95-7.03 (m, 2H), 6.85 (d, J=8.4 Hz, 1H), 5.64-5.78 (m, 1H), 3.88 (s, 3H), 3.65 (dd, J=12.9, 6.8 Hz, 2H), 2.85 (t, J=6.9 Hz, 2H), 2.37 (s, 3H), 2.31 (s, 3H).

Step 3—Synthesis of 6-bromo-1-(2,4-dimethylphenyl)-7-methoxy-3,4-dihydroisoquinoline

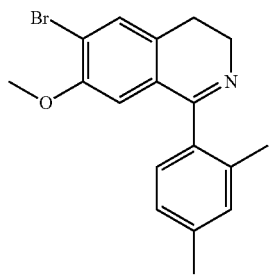

Over a solution of N-(3-bromo-4-methoxyphenethyl)-2,4-dimethylbenzamide (0.32 g, 0.88 mmol) in dry acetonitrile (7 mL) was added POCl₃ and the mixture was stirred at reflux. After 4 h the reaction mixture was concentrated under vacuo to obtain the crude product (298 mg, 98% yield) which was immediately used without further purification.

Step 4—Synthesis of 6-bromo-1-(2,4-dimethylphenyl)-7-methoxy-3,4-dihydroisoquinoline

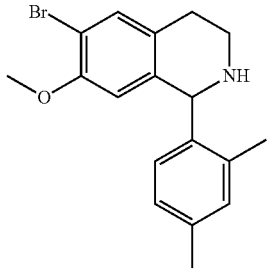

To a solution of 6-bromo-1-(2,4-dimethylphenyl)-7-methoxy-3,4-dihydroisoquinoline (298 mg, 0.87 mmol) in methanol (10 mL), sodium borohydride (328 mg, 8.66 mmol) was added in portions. The mixture was stirred at room temperature for 2 h. The solvent was evaporated under vacuo and excess reagent remaining in the residue was decomposed with water and extracted with ethyl acetate. The extract was washed with water, dried over anhydrous MgSO₄, filtered and concentrated to give the product as a beige solid (300 mg, 99% yield). ¹H NMR (400 MHz, CDCl₃) δ ppm 7.21 (s, 1H), 6.99 (d, J=7.5 Hz, 1H), 6.98 (d, J=1.5 Hz, 1H), 6.92 (dd, J=7.5, 1.5 Hz, 1H), 6.85 (s, 1H), 5.19 (s, 1H), 3.83 (s, 3H), 3.25-3.35 (m, 2H), 2.75-2.79 (m, 2H), 2.34 (s, 6H), 1.91 (bs, 1H).

Step 5—Synthesis of tert-butyl 6-bromo-1-(2,4-dimethylphenyl)-7-methoxy-3,4-dihydroisoquinoline-2(1H)-carboxylate

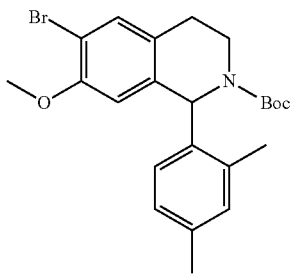 [SMILES: COc1cc2c(cc1Br)CCN(C(=O)OC(C)(C)C)C2c1ccc(C)cc1C]

To a stirred suspension of 6-bromo-1-(2,4-dimethylphenyl)-7-methoxy-3,4-dihydroisoquinoline (300 mg, 0.87 mmol) in water (3.8 mL) was added TEA (0.6 mL, 4.35 mmol) and di-tert-butyl dicarbonate (192 mg, 0.87 mmol) drop by drop at 0° C. (ice bath). The mixture was stirred at r.t. for 30 minutes. Then, water was added and the product was extracted with ethyl acetate. The residue was purified by column chromatography on silica gel (Ethyl acetate: Hexane=20:80) to give the title compound as a beige solid (361 mg, 93% yield). ¹H NMR (400 MHz, CDCl₃) δ ppm 7.21 (s, 1H), 6.99 (d, J=7.5 Hz, 1H), 6.98 (d, J=1.5 Hz, 1H), 6.92 (dd, J=7.5, 1.5 Hz, 1H), 6.85 (s, 1H), 6.28 (s, 1H), 3.83 (s, 3H), 3.24-3.34 (m, 2H), 2.90-2.93 (m, 2H), 2.34 (s, 6H), 1.38 (s, 9H)

Step 6—Synthesis of 2-tert-butyl 6-methyl 1-(2,4-dimethylphenyl)-7-methoxy-3,4-dihydroisoquinoline-2,6(1H)-dicarboxylate

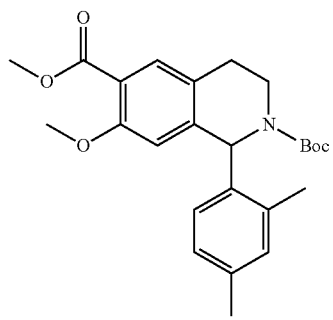 [SMILES: COC(=O)c1cc2c(cc1OC)C(c1ccc(C)cc1C)N(C(=O)OC(C)(C)C)CC2]

Tert-butyl 6-bromo-1-(2,4-dimethylphenyl)-7-methoxy-3,4-dihydroisoquinoline-2(1H)-carboxylate (361 mg, 0.81 mmol), Pd(dppf)Cl$_2$ (59 mg, 0.08 mmol) and triethylamine (0.34 mL, 2.43 mmol) in methanol (8 mL) were stirred at 100° C. under CO atmosphere (100 psi). After 5 h the reaction mixture was concentrated under vacuo and the residue purified by column chromatography on silica gel (Ethyl acetate:Hexane=20:80) to give the title compound as a beige solid (300 mg, 87% yield). $^1$H NMR (400 MHz, CDCl$_3$) δ 7.59 (s, 1H), 7.07 (s, 1H), 6.92-6.98 (m, 3H), 6.28 (s, 1H), 3.89 (s, 3H), 3.83 (s, 3H), 3.24-3.34 (m, 2H), 2.90-2.93 (m, 2H), 2.34 (s, 6H), 1.38 (s, 9H).

Step 7—Synthesis of methyl 1-(2,4-dimethylphenyl)-7-methoxy-1,2,3,4-tetrahydroisoquinoline-6-carboxylate hydrochloride

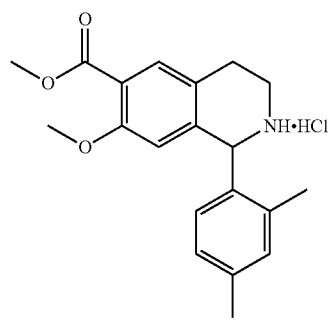

Over a solution of 2-tert-butyl 6-methyl 1-(2,4-dimethylphenyl)-7-methoxy-3,4-dihydroisoquinoline-2,6(1H)-dicarboxylate (300 mg, 0.70 mmol) in dioxane (1.2 mL) was added a solution of HCl 4.0 M in dioxane (4 mL, 16.8 mmol). The reaction mixture was stirred at 55° C. After 2 h the solvent was evaporated under vacuo to yield the crude product as a chlorhydrate salt (252 mg, 100% yield). $^1$H NMR (400 MHz, CD$_3$OD) δ ppm 7.59 (s, 1H), 7.07 (s, 1H), 6.99 (d, J=7.5 Hz, 1H), 6.98 (d, J=1.5 Hz, 1H), 6.92 (dd, J=7.5, 1.5 Hz, 1H), 5.19 (s, 1H), 3.89 (s, 3H), 3.83 (s, 3H), 3.25-3.35 (m, 2H), 2.75-2.79 (m, 2H), 2.34 (s, 6H).

Step 8—Synthesis of methyl 1-(2,4-dimethylphenyl)-7-methoxy-2-((oxazol-4-ylmethyl)carbamoyl)-1,2,3,4-tetrahydroisoquinoline-6-carboxylate

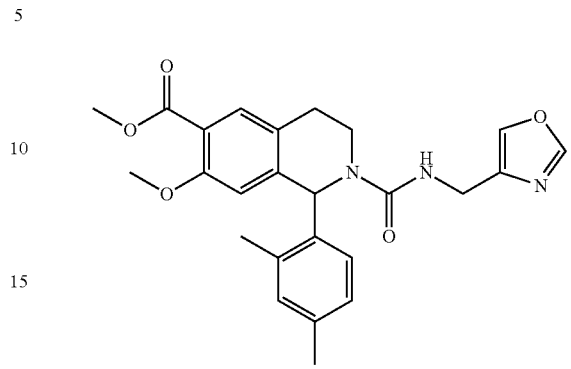

To a suspension of oxazol-4-ylmethanamine dihydrochloride (398 mg, 2.81 mmol) in dry dimethylformamide (2 mL) was added triethylamine (0.78 mL, 5.6 mmol). The mixture was stirred at room temperature for 10 min, after which time was added carbonyldiimidazole (257 mg, 1.4 mmol). The mixture was stirred at room temperature for 1 h, after which time was added methyl 1-(2,4-dimethylphenyl)-7-methoxy-1,2,3,4-tetrahydroisoquinoline-6-carboxylate hydrochloride (252 mg, 0.70 mmol) dissolved in dry dimethylformamide (3.8 mL). The reaction was stirred at room temperature. After 4 h, the reaction mixture was partitioned between ethyl acetate and water. The organic layer was washed with brine, dried over anhydrous MgSO$_4$, filtered and concentrated under vacuo. The residue was purified by reverse phase chromatography (acetonitrile/water 0-100% gradient) to give the title product as a white solid (189 mg, 60% yield). $^1$H NMR (400 MHz, CDCl$_3$) δ ppm 7.95 (s, 1H), 7.69 (s, 1H), 7.59 (s, 1H), 7.07 (s, 1H), 6.92-6.98 (m, 3H), 6.28 (s, 1H), 6.01 (bs, 1H), 4.10 (s, 2H), 3.89 (s, 3H), 3.83 (s, 3H), 3.44-3.54 (m, 2H), 2.90-2.93 (m, 2H), 2.34 (s, 6H).

Step 9—Synthesis of methyl 1-(2,4-dimethylphenyl)-7-hydroxy-2-((oxazol-4-ylmethyl)carbamoyl)-1,2,3,4-tetrahydroisoquinoline-6-carboxylate

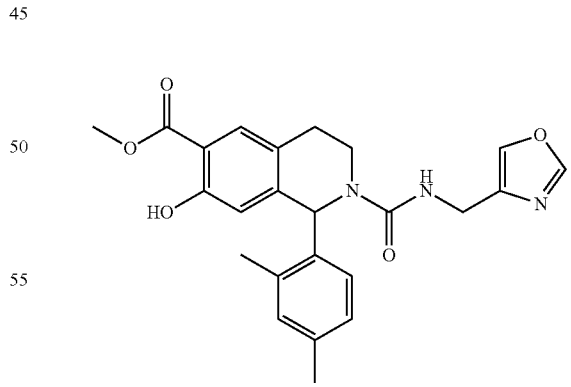

To a solution of methyl 1-(2,4-dimethylphenyl)-7-methoxy-2-((oxazol-4-ylmethyl)carbamoyl)-1,2,3,4-tetrahydroisoquinoline-6-carboxylate (189 mg, 0.42 mmol) in anhydrous dichloromethane (2.3 mL) was added boron tribromide 1.0 M in methylene chloride (0.84 mL, 0.84 mmol) dropwise at −78° C. The reaction mixture was stirred overnight at room temperature and quenched by ice. The resulting mixture was extracted by ethyl acetate. The combined organic layers were dried over anhydrous MgSO₄ and concentrated in vacuo to yield the product as a brown solid (135 mg, 74% yield). ¹H NMR (400 MHz, CDCl₃) δ ppm 7.95 (s, 1H), 7.69 (s, 1H), 7.53 (s, 1H), 6.92-7.03 (m, 4H), 6.28 (s, 1H), 6.01 (bs, 1H), 5.35 (bs, 1H), 4.10 (s, 2H), 3.89 (s, 3H), 3.44-3.54 (m, 2H), 2.90-2.93 (m, 2H), 2.34 (s, 6H).

Step 10—Synthesis of methyl 1-(2,4-dimethylphenyl)-2-((oxazol-4-ylmethyl)carbamoyl)-7-(2-(pyridin-3-yl)ethoxy)-1,2,3,4-tetrahydroisoquinoline-6-carboxylate

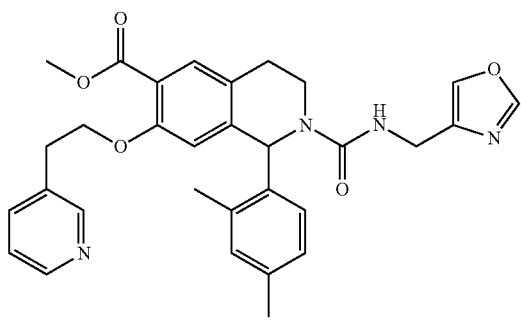 [SMILES: COC(=O)c1cc2c(cc1OCCc1cccnc1)C(c1ccc(C)cc1C)N(C(=O)NCc1cocn1)CC2]

To a solution of 2-(pyridin-3-yl)ethanol (38 mg, 0.31 mmol) in dry tetrahydrofuran (1.2 mL), methyl 1-(2,4-dimethylphenyl)-7-hydroxy-2-((oxazol-4-ylmethyl)carbamoyl)-1,2,3,4-tetrahydroisoquinoline-6-carboxylate (135 mg, 0.31 mmol) and triphenylphosphine (107 mg, 0.4 mmol) were added, followed by the slow addition of diisopropylazodicarboxylate (84 μL, 0.4 mmol). The reaction was stirred at room temperature for 2 h. The solvent was evaporated under vacuo and the residue purified by column chromatography on silica gel (Ethyl Acetate:Hexane=20:80) to give the title compound as a white solid (90 mg, 54% yield). ¹H NMR (400 MHz, CDCl₃) δ ppm 8.41-8.43 (m, 2H), 7.95 (s, 1H), 7.67-7.69 (m, 2H), 7.59 (s, 1H), 7.25 (t, J=7.5 Hz, 1H), 7.07 (s, 1H), 6.92-6.98 (m, 3H), 6.28 (s, 1H), 6.01 (bs, 1H), 4.27 (t, J=7.1 Hz, 2H), 4.10 (s, 2H), 3.89 (s, 3H), 3.44-3.54 (m, 2H), 2.93-3.00 (m, 4H), 2.34 (s, 6H).

Step 11—Synthesis of 1-(2,4-dimethylphenyl)-2-((oxazol-4-ylmethyl)carbamoyl)-7-(2-(pyridin-3-yl)ethoxy)-1,2,3,4-tetrahydroisoquinoline-6-carboxylic acid hydrochloride

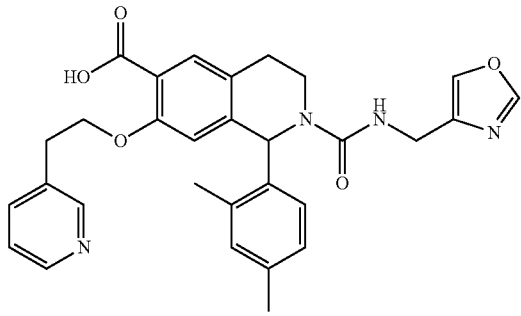 [SMILES: Cc1ccc(C2c3cc(OCCc4cccnc4)c(C(=O)O)cc3CCN2C(=O)NCc2cocn2)c(C)c1]

Over a solution of methyl 1-(2,4-dimethylphenyl)-2-((oxazol-4-ylmethyl)carbamoyl)-7-(2-(pyridin-3-yl)ethoxy)-1,2,3,4-tetrahydroisoquinoline-6-carboxylate (90 mg, 0.166 mmol) in THF (8.3 mL) and water (830 μL), lithium hydroxide (8 mg, 0.33 mmol) was added. The reaction mixture was stirred at room temperature. After 2 h water (8 mL) was added to dilute the reaction mixture, the organic solvent was evaporated under vacuo and the aqueous residue was acidified (pH=5) by addition of 1N HCl. Extraction with ethyl acetate was carried out to obtain the product as clorhydrate salt (90 mg, 96% yield). ¹H NMR (400 MHz, CDCl₃) δ ppm 11.0 (bs, 1H), 8.41-8.43 (m, 2H), 7.95 (s, 1H), 7.75 (s, 1H), 7.67-7.69 (m, 2H), 7.25 (t, J=7.5 Hz, 1H), 7.17 (s, 1H), 6.92-6.98 (m, 3H), 6.28 (s, 1H), 6.01 (bs, 1H), 4.27 (t, J=7.1 Hz, 2H), 4.10 (s, 2H), 3.44-3.54 (m, 2H), 2.90-3.00 (m, 4H), 2.34 (s, 6H).

Step 12—Synthesis of 1-(2,4-dimethylphenyl)-N2-(oxazol-4-ylmethyl)-7-(2-(pyridin-3-yl)ethoxy)-3,4-dihydroisoquinoline-2,6(1H)-dicarboxamide

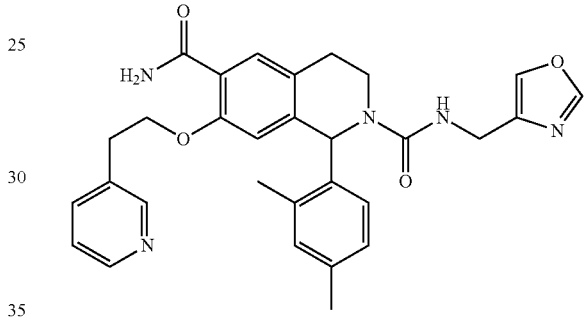

1-Ethyl-3-(3-dimethylaminopropyl)carbodiimide hydrochloride (61 mg, 0.32 mmol) and N,N-diisopropylethylamine (84 μL, 0.48 mmol) were added to a solution of ammonium chloride (43 mg, 0.8 mmol), 1-(2,4-dimethylphenyl)-2-((oxazol-4-ylmethyl)carbamoyl)-7-(2-(pyridin-3-yl)ethoxy)-1,2,3,4-tetrahydroisoquinoline-6-carboxylic acid hydrochloride (90 mg, 0.16 mmol) and 1-hydroxybenzotriazole hydrate (22 mg, 0.16 mmol) in dry N,N-dimethylformamide. After 24 h the reaction mixture was partitioned between ethyl acetate and water. The organic layer was dried over anhydrous MgSO₄, filtered and concentrated under vacuo. The residue was purified by reverse phase chromatography (acetonitrile/water 0-100% gradient) to give the title product as a white solid (49 mg, 58% yield). ¹H NMR (400 MHz, CDCl₃) δ ppm 8.41-8.43 (m, 2H), 7.95 (s, 1H), 7.67-7.69 (m, 2H), 7.57 (s, 1H), 7.50 (bs, 2H), 7.25 (t, J=7.5 Hz, 1H), 6.92-6.98 (m, 3H), 6.28 (s, 1H), 6.01 (bs, 1H), 4.27 (t, J=7.1 Hz, 2H), 4.10 (s, 2H), 3.44-3.54 (m, 2H), 2.90-3.00 (m, 4H), 2.34 (s, 6H).

In addition to compound 34, compounds 24, 28, 32, 33 and 35-45 may also be prepared according to schemes 4 or 4b.

Example 3—Activity in Tumor Cell Lines

Cell line #1: A549. Lung carcinoma cell line bearing KRas$^{G12S}$ oncogenic mutation
Cell line #2: H358. non-small cell lung cancer line bearing KRas$^{G12C}$ oncogenic mutation
Cell line #3: PANC-1. epithelioid carcinoma of the pancreas cell line bearing KRas$^{G12D}$ oncogenic mutation Cell line #4: RPMI. myeloma cell line bearing KRas$^{G12A}$ oncogenic mutation Cell lines were cultured in DMEM or RPMI-1640 supplemented with FBS 10%. In order to assess the antiproliferative effect of compounds, cells were seeded at a density of $1.8\times10^3$, $6.2\times10^3$, $7.8\times10^3$, $21\times10^3$ and $2\times10^3$ cells/cm$^2$, respectively, in tissue culture microplates and were incubated in humidified atmosphere at 5% $CO_2$. 24 h later, compounds dissolved in DMSO 100% were added for different final concentrations ranging between 0.1 and 50 µM for a final DMSO concentration of 0.5% and the plates were incubated for another 72 h. After incubation, proliferation was quantified using CellTiter 96® Aqueous Non-Radioactive Cell Proliferation Assay-MTS (Promega #G5421) following manufacturer instructions. Amount of 490 nm absorbance is directly proportional to the number of living cells. Absorbance was recorded with a BMG Fluostar Optima Microplate Reader and normalized to control with vehicle.

| IC50 values (µM): cell proliferation inhibition | | | | |
|---|---|---|---|---|
| Compound | A549 | RPMI-8226 | H358 | PANC-1 |
| 1 | 11.73 | 2.17 | 18.31 | 17.26 |
| 2 | 8.25 | 1.8 | 12.12 | 17.29 |
| 3 | 1.97 | 1.21 | 1.66 | 1.59 |
| 4 | 10.09 | 2.67 | >20 | 29.67 |
| 5 | 4.82 | 1.51 | >20 | >30 |
| 6 | 9.09 | 5.65 | 19.94 | 24.72 |
| 7 | 6.34 | 2.41 | 18.1 | 24.77 |
| 8 | 4.11 | 2.11 | 11.22 | 11.11 |
| 9 | 3.65 | 0.74 | 18.95 | 24.50 |
| 10 | 15.87 | 0.86 | 19.76 | 15.03 |
| 11 | 18.03 | 1.47 | 8.52 | 12.27 |
| 12 | 8.99 | 4.98 | 16.82 | 13.59 |
| 13 | 9.37 | 2.86 | 15.75 | 12.59 |
| 14 | >10 | 3.94 | >10 | >30 |
| 15 | 2.14 | 0.89 | 2.58 | 2.13 |
| 16 | >5 | 0.48 | 7.24 | 11.97 |
| 17 | 3.52 | 1.74 | 3.10 | 1.83 |
| 18 | 1.97 | 1.21 | 1.66 | 1.59 |
| 19 | 0.95 | 2.93 | 0.68 | 0.57 |
| 20 | 0.75 | 0.60 | 0.48 | 0.56 |
| 21 | 1.33 | 0.90 | 0.78 | 0.81 |
| 22 | 0.89 | 0.82 | 0.65 | 0.60 |
| 23 | 0.55 | 0.62 | 0.59 | 0.49 |
| 24 | 0.74 | 0.87 | 0.84 | 0.66 |
| 25 | 0.55 | 0.58 | 0.52 | 0.53 |
| 26 | 2.02 | 0.79 | 1.01 | 1.15 |
| 27 | 1.02 | 0.98 | 1.12 | 1.33 |
| 28 | 1.56 | 1.02 | 1.23 | 2.01 |
| 29 | 0.76 | 0.69 | 0.96 | 0.68 |
| 30 | 1.47 | 1.21 | 1.41 | 2.11 |
| 31 | 2.07 | 1.91 | 2.11 | 1.83 |
| 32 | 0.44 | 0.52 | 0.31 | 0.49 |
| 33 | 1.57 | 1.31 | 1.04 | 2.03 |
| 34 | 0.43 | 0.72 | 0.39 | 0.42 |
| 35 | 0.33 | 0.32 | 0.51 | 0.43 |
| 36 | 0.73 | 0.99 | 0.91 | 0.67 |
| 37 | 0.81 | 1.21 | 0.71 | 0.74 |
| 38 | 0.43 | 0.22 | 1.09 | 0.42 |
| 39 | 0.34 | 0.41 | 0.52 | 0.47 |
| 40 | 0.82 | 1.33 | 0.96 | 0.81 |
| 41 | 1.27 | 1.38 | 1.14 | 2.11 |
| 42 | 0.49 | 0.32 | 1.21 | 0.62 |
| 43 | 0.74 | 0.61 | 0.91 | 0.88 |
| 44 | 1.72 | 0.99 | 1.01 | 1.00 |
| 45 | 0.79 | 0.89 | 0.99 | 0.87 |
| 46 | 0.6 | 0.5 | 0.7 | 0.7 |
| 47 | 1.5 | 1.5 | 1.2 | 1.5 |
| 48 | 0.7 | 0.9 | 0.8 | 0.7 |
| 49 | >1 | >1 | >1 | >1 |
| 50 | 0.8 | 0.8 | 0.8 | 0.5 |
| 51 | 0.5 | 0.6 | 0.6 | 0.5 |
| 52 | 0.6 | 0.7 | 0.6 | 0.5 |
| 53 | 0.6 | 0.5 | 0.7 | 0.7 |
| 54 | 0.6 | 0.5 | 0.7 | 0.7 |
| 55 | 0.6 | 0.6 | 0.6 | 0.5 |
| 56 | 0.6 | 0.6 | 0.6 | 0.5 |
| 57 | 0.6 | 0.6 | 0.6 | 0.5 |
| 58 | 0.6 | 0.6 | 0.6 | 0.5 |
| 59 | 0.6 | 0.5 | 0.7 | 07 |
| 60 | 0.6 | 0.5 | 0.7 | 0.7 |
| 61 | 0.6 | 0.5 | 0.7 | 0.7 |
| 62 | 0.6 | 0.5 | 0.7 | 0.7 |
| 63 | 0.6 | 0.5 | 0.7 | 0.7 |

Data shown for compounds 1-53 are the median from experimental results. Data shown for compounds 54-63 are based on estimations and/or preliminary experimental results.

Example 4—Activity in Mouse Xenografts

Evaluation of the Efficacy of compound 18 in the Treatment of Subcutaneous NCI-H358 Human Lung Cancer Xenograft Model in NOD/SCID Mice Experimental Design The treatments were started when the mean tumor size reached 141 mm$^3$. The test article administration and the animal numbers in each study group are shown in the following experimental design table.

| Group | N | Treatment | Dose (mg/kg) | Dosing | Schedule |
|---|---|---|---|---|---|
| 1 | 6 | Vehicle Control | — | i.p. | Bid × 22 day |
| 2 | 6 | Compound 18 | 10 | i.p. | Bid × 22 day |
| 3 | 6 | cisplatin | 3.5 | i.p. | BIW × 3.5 week |

Note:

N: animal number;

Dosing volume: 10 µl/g

Study endpoints: The major endpoints of the study included the followings:

Tumor growth inhibition (TGI): TGI (%) is an indication of antitumor effectiveness, and expressed as: TGI (%)=100× (1−T/C). T and C were the mean tumor volume of the treated and control groups, respectively, on a given day.

The results of the body weight changes in the tumor bearing mice are shown in Figure 1. The body weight loss (BWL) of just one mouse reached 10% in group 2 (compound 18, 10 mg/kg), while the BWL of 4 mice in group 3 (Cisplatin, 3.5 mg/kg) reached 10% or even lower. The results suggest that the mice bearing the subcutaneous NCI-H358 human lung cancer xenograft model tolerate 10 mg/kg b.i.d of Compound 18.

Figure 2:
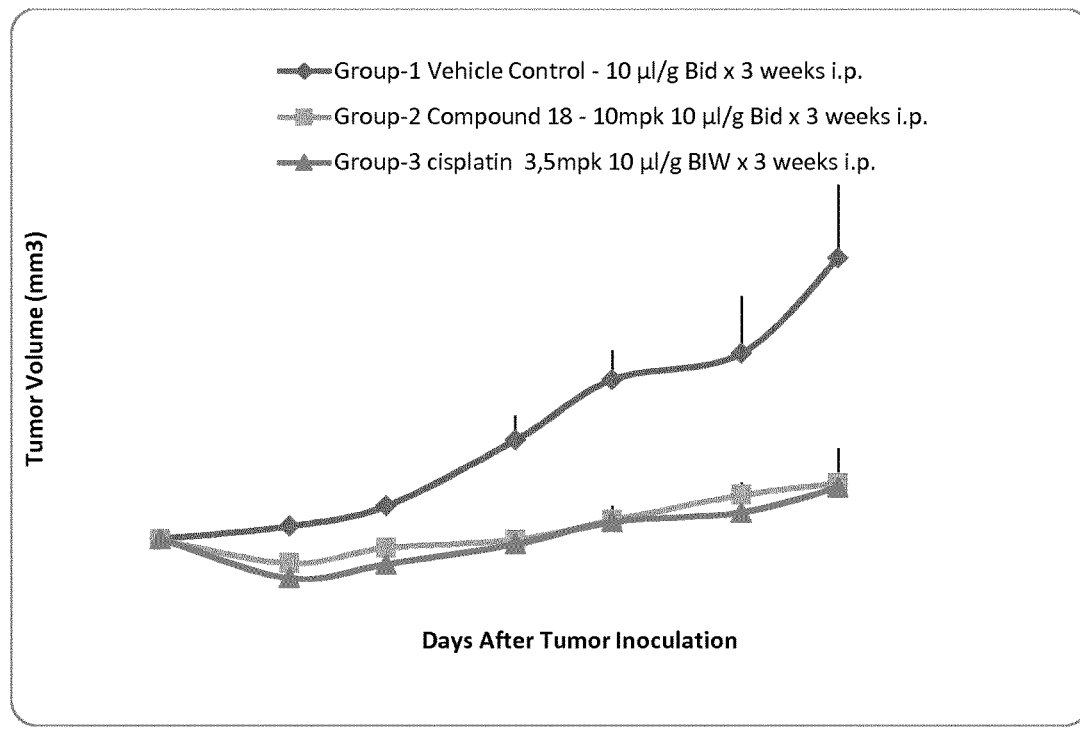

The tumor growth curves of the different groups are shown in Figure 2.

The mean tumor volume of group-1 (vehicle) reached 630 mm$^3$ on Day 24 after inoculation (PG-D22, Day 22 after first-dosing). The mean tumor volume of group-2 (Compound 18, 10 mg/kg) reached 238 mm$^3$ on PG-D22, and TGI is about 62%. The mean tumor volume of group-3 (Cisplatin, 3.5 mg/kg) reached 231 mm$^3$ on PG-D22, and TGI is about 63%. Compared with the vehicle group, groups 2 and 3 both exhibit significant anti-tumor effects (group-2 p=0.026, group-3 p=0.019).

The test compound 18 demonstrated significant antitumor activities in subcutaneous NCI-H358 human lung cancer xenograft model, and 10 mg/kg b.i.d. of compound 18 is safe for the bearing mice.

Example 5: Determination of Equilibrium Dissociation Constant (KD) Using Surface Plasmon Resonance The KD for Compound 18 is 8.8 nM (Ka=$1.17 \times 10^5$ $M^{-1} \cdot s^{-1}$; Kd=$1.03 \times 10^{-3} s^{-1}$)

The protocol to determine KD is as follows:

Various concentrations of KRas dissolved in water were manually printed onto bare gold-coated (thickness 47 nm) PlexArray Nanocapture Sensor Chips (Plexera Bioscience, Seattle, Wash., US) at 40% humidity. Each concentration was printed in replicate, and each spot contained 0.2 μL of KRas solution. The chip was incubated in 80% humidity at 4° C. for overnight, and rinsed with 10×PBST for 10 min, 1×PBST for 10 min, and deionized water twice for 10 min. The chip was then blocked with 5% (w/v) non-fat milk in water overnight, and washed with 10×PBST for 10 min, 1×PBST for 10 min, and deionized water twice for 10 min before being dried under a stream of nitrogen prior to use. SPRi measurements were performed with PlexAray HT (Plexera Bioscience, Seattle, Wash., US). Collimated light (660 nm) passes through the coupling prism, reflects off the SPR-active gold surface, and is received by the CCD camera. Buffers and samples were injected by a non-pulsatile piston pump into the 30 μL flowcell that was mounted on the coupling prim. Each measurement cycle contained four steps: washing with PBST running buffer at a constant rate of 2 μL/s to obtain a stable baseline, Compound 18 injection at 5 uL/s for binding, surface washing with PBST at 2 μL/s for 300 s, and regeneration with 0.5% (v/v) H3PO4 at 2 μL/s for 300 s. All measurements were performed at 4° C. The signal changes after binding and washing (in AU) are recorded as the assay value. Selected protein-grafted regions in the SPR images were analyzed, and the average reflectivity variations of the chosen areas were plotted as a function of time. Real-time binding signals were recorded and analyzed by Data Analysis Module (DAM, Plexera Bioscience, Seattle, Wash., US). Kinetic analysis was performed using BIAevaluation 4.1 software (Biacore, Inc.).

Example 6: Efficacy Testing in 3D Viability Assay for NIH-H358 Cell Line

The protocol to perform 3D CellTiter-Glo™ cell viability assay is as follows:

Day −1: Cell Plating

Adjust cell concentrations to 1×105 cells/ml with respective medium. (Cell concentration is adjusted according to data base or density optimization assay). Mix 3.5 mL of cell suspension 6.5 mL of 1% methylcellulose. Mix and wait for bubbles to disperse before pipetting. This step yields 10 ml of cell suspension in 0.65% methylcellulose solution. Add 99.5 μL cell suspensions to 96-well plates according to plate map with final cell density.

Two duplicate plates will be set up. One is for day 0 reading (T0) and the other will be cultured in incubator for reading at the end point.

Incubate the plates overnight in humidified incubator at 37° C. with 5% CO2.

Day 0: T0 plate reading and compound treatment

Take T0 plate, add 0.5 μL culture medium to each well for T0 reading.

Add 100 μl CellTiter-Glo® Reagent to each well.

Mix contents for 2 minutes on an orbital shaker to facilitate cell lysis.

Allow the plate to incubate at room temperature for 10 minutes to stabilize luminescent signal.

Record luminescence using EnVision Multi Label Reader.

Dilute the test articles at the concentration indicated at Test Articles Dilution. Add 0.5 μL of each 200× compound working solutions according to plate inoculation map.

Day 7: Plate reading of 7 days' compound treatment

Add 100 μL CellTiter-Glo® Reagent to each well.

Mix contents for 2 minutes on an orbital shaker to facilitate cell lysis.

Allow the plate to incubate at room temperature for 10 minutes to stabilize luminescent signal.

Record luminescence using EnVision Multi Label Reader.

Results:

| Compound | IC50 (μM) |
|---|---|
| 17 | 0.62 |
| 18 | 0.37 |
| 23 | 0.39 |
| 26 | 9.351 |
| 42 | 10.057 |
| 46 | 0.842 |
| 48 | 0.917 |
| 50 | 0.373 |
| 51 | 0.334 |

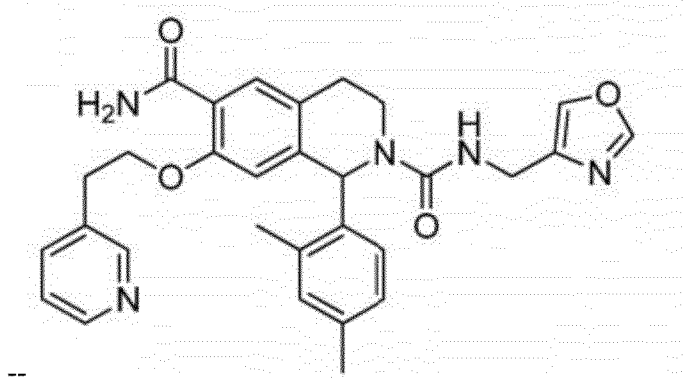

The invention claimed is:

1. A compound of Formula I, enantiomers and pharmaceutically acceptable salts thereof:

Formula I

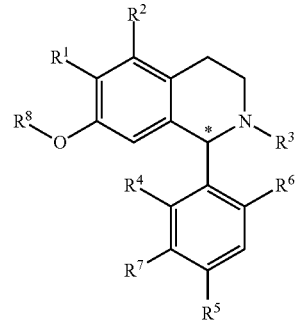

wherein:

$R^1$ is $(R^y)_{k^1}$-$(Y^1)_{n^1}$—$(X_1)_{m^1}$—$R^x$, $(R^y)_{k^1}$—$(X_1)_{m^1}$—$(Y^1)_{n^1}$—$R_x$ or halogen;

$Y^1$ is C(O) or S(O)$_2$;

$X^1$ is NH or O;

$R^y$ is $C_{1-4}$ alkanediyl, $C_{2-4}$ alkenediyl or $C_{2-4}$ alkynediyl;

$R^x$ is $C_{1-4}$ alkyl, $C_{2-4}$ alkenyl, $C_{2-4}$ alkynyl, or H;

$k^1$ is 0 or 1;

$n^1$ is 0 or 1;

$m^1$ is 0 or 1;

$R^2$ is H, $C_{1-4}$ alkyl, $C_{2-4}$ alkenyl, $C_{2-4}$ alkynyl, halogen, $OC_{1-4}$ alkyl, $OC_{2-4}$ alkenyl, or $OC_{2-4}$ alkynyl;

$R^3$ is —$(CH_2)_{n^3}$—$C(Y^3)$—$(X^3)_{m^3}$—$(CH_2)_{k^3}$—$R^{3a}$;

$n^3$ is an integer in the range of 0 to 2;

$Y^3$ is S or O;

$X^3$ is S, NH, or O, $m^3$ is 0 or 1;
$k^3$ is 0 or 1;
$R^{3a}$ is $C_{1-4}$ alkyl, $C_{2-4}$ alkenyl, $C_{2-4}$ alkynyl, $OC_{1-4}$ alkyl, $OC_{2-4}$ alkenyl, $OC_{2-4}$ alkynyl, $Het^3$, $Ar^3$, $HetCyc^3$ or $Cyc^3$;
wherein:
  $Het^3$ is a 5- to 10-membered heteroaromatic ring or ring system containing one or more heteroatoms selected from the group consisting of N, O, and S;
  $Ar^3$ is a 6- to 10-membered aromatic ring or ring system;
  $HetCyc^3$ is a 3- to 8-membered heterocyclyl containing one or more heteroatoms selected from the group consisting of N, O, and S; and
  $Cyc^3$ is a 3- to 8-membered cyclyl,
$R^4$ is halogen, $OC_{1-4}$ alkyl, $OC_{2-4}$ alkenyl, $OC_{2-4}$ alkynyl, $C_{1-4}$ alkyl, $C_{2-4}$ alkenyl or $C_{2-4}$ alkynyl;
$R^5$ is hydrogen, $OC_{1-4}$ alkyl, $OC_{2-4}$ alkenyl, $OC_{2-4}$ alkynyl, OH, $C_{1-4}$ alkyl, $C_{2-4}$ alkenyl, or $C_{2-4}$ alkynyl, wherein each $C_{1-4}$ alkyl, $C_{2-4}$ alkenyl, or $C_{2-4}$ alkynyl independently optionally substituted with 1 to 3 halogens;
$R^6$ is H, OH, halogen, or $NH_2$;
$R^7$ is H, halogen, OH, $C_{1-4}$ alkyl, $C_{2-4}$ alkenyl, $C_{2-4}$ alkynyl, $OC_{1-4}$ alkyl, $OC_{2-4}$ alkenyl, or $OC_{2-4}$ alkynyl;
$R^8$ is —$(CH_2)_{n^8}$—$(C(O))_{m^8}$—$R^{8a}$;
$n^8$ is an integer from 1 to 2;
$m^8$ is an integer from 0 to 1;
$R^{8a}$ is an aromatic or heteroaromatic ring having 5 or 6 ring members, optionally substituted with at least 1 substituent selected from the group consisting of OH, $C_{1-4}$ alkyl, $C_{2-4}$ alkenyl, $C_{2-4}$ alkynyl, $OC_{1-4}$ alkyl, $OC_{2-4}$ alkenyl, $OC_{2-4}$ alkynyl, $CO_2$—$C_{1-4}$ alkyl, $CO_2$—$C_{2-4}$ alkenyl, $CO_2$—$C_{2-4}$ alkynyl, halogen, $CONH_2$, CN, COOH, —OCO—$C_{1-4}$ alkyl, —OCO—$C_{2-4}$ alkenyl, —OCO—$C_{2-4}$ alkynyl, —NHCO—$C_{1-4}$ alkyl, —NHCO—$C_{2-4}$ alkenyl, —NHCO—$C_{2-4}$ alkynyl, $NH_2$, $NHC_{1-4}$ alkyl, $NHC_{2-4}$ alkenyl, $NHC_{2-4}$ alkynyl, $N(C_{1-4}$ alkyl$)_2$, $N(C_{2-4}$ alkenyl$)_2$, $N(C_{2-4}$ alkynyl$)_2$, $CONHC_{1-4}$ alkyl, $CONHC_{2-4}$ alkenyl, $CONHC_{2-4}$ alkynyl, $CON(C_{1-4}$ alkyl$)_2$, $CON(C_{2-4}$ alkenyl$)_2$, and $CON(C_{2-4}$ alkynyl$)_2$;
$R^{8a}$ is an aromatic or heteroaromatic ring having 5 or 6 ring members fused with an additional optionally substituted cyclic, heterocyclic, aromatic, or heteroaromatic ring.

2. The compound according to claim 1 wherein:
$R^{8a}$ is a phenyl ring, optionally substituted with at least 1 substituent selected from the group consisting of OH, $C_{1-4}$ alkyl, $OC_{1-4}$ alkyl, $CO_2$—$C_{1-4}$ alkyl, halogen, $CONH_2$, CN, and COOH.

3. The compound according to claim 2, wherein the phenyl ring is substituted in the meta position.

4. The compound according to claim 1, wherein $R^{8a}$ is optionally substituted pyridinyl, indanyl, 2,3-dihydro-benzofuran-5-yl, or pyrymidino[1,2-b][1,2,4]triazol-3-yl.

5. The compound according to claim 1, wherein $Y^3$ is O and $X^3$ is NH.

6. The compound according to claim 5, wherein $n^3$ is 0 and $m^3$ is 1.

7. The compound according to claim 5, wherein $R^{3a}$ is oxazolyl or pyridinyl.

8. The compound according to claim 1, wherein $n^3$ is 2 and $m^3$ is 0.

9. The compound according to claim 5, wherein $k^3$ is 1.

10. The compound according to claim 1, wherein $R^2$ is H.

11. The compound according to claim 1, wherein $R^6$ and $R^7$ are H.

12. The compound according to claim 1 which is selected from.

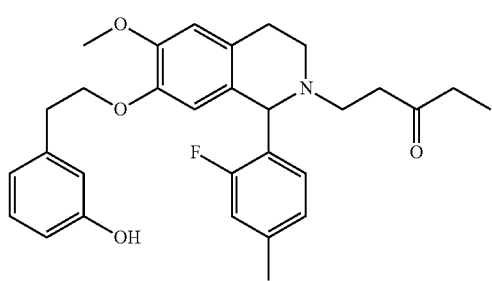
6
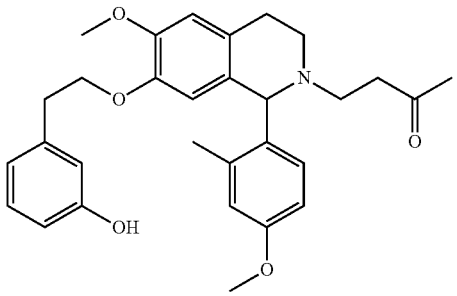
11
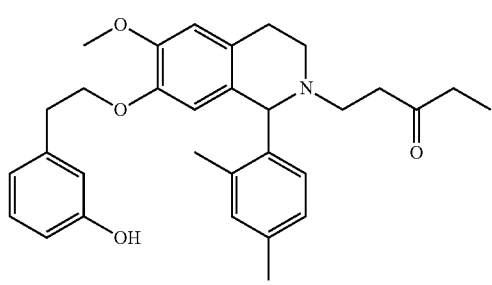
7
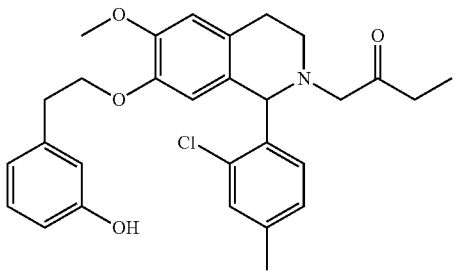
12
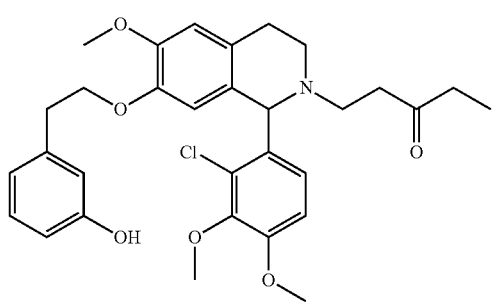
8
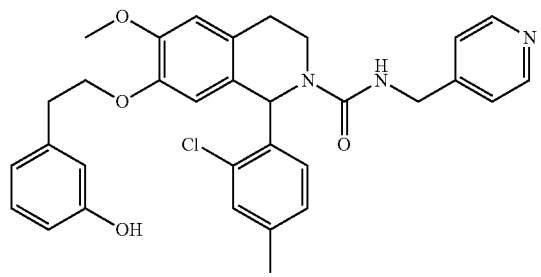
13
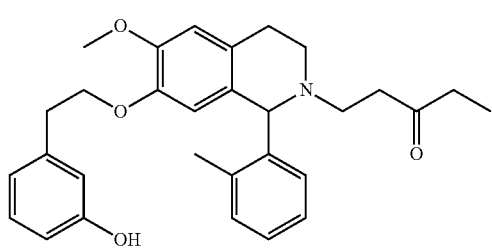
9
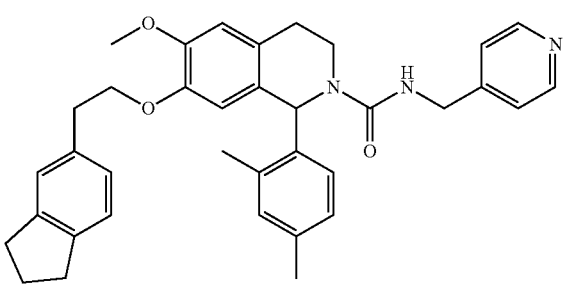
14
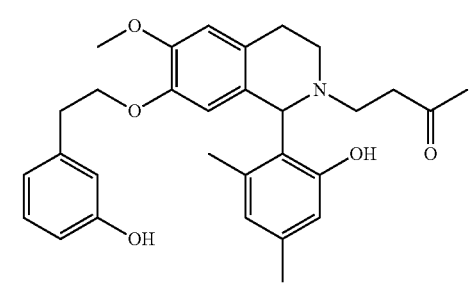
10
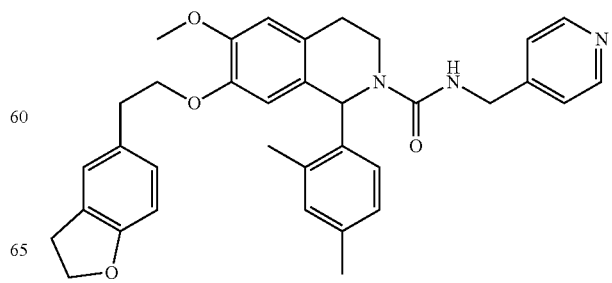
15

16
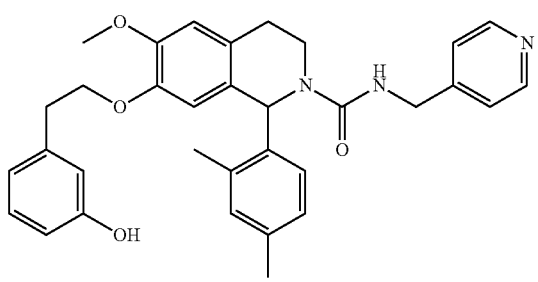
17
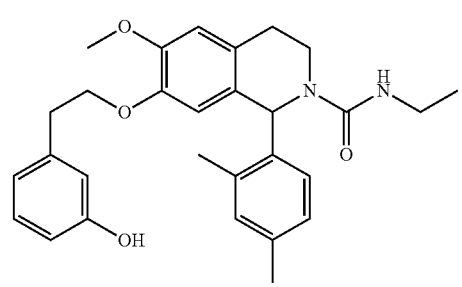
18
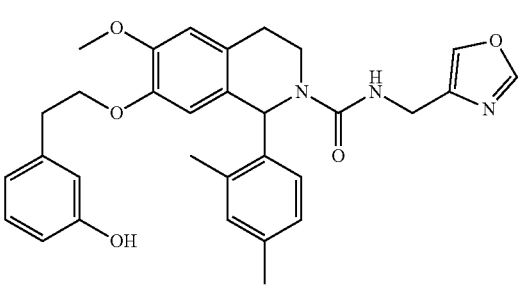
19
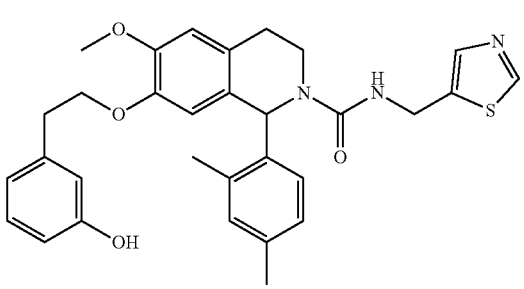
20
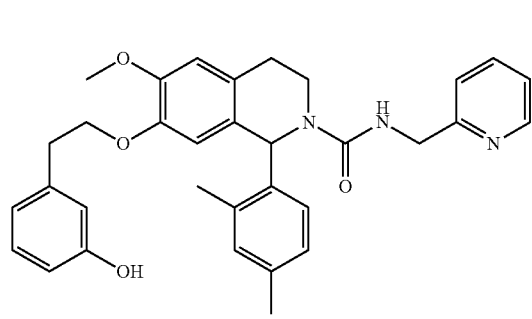
21
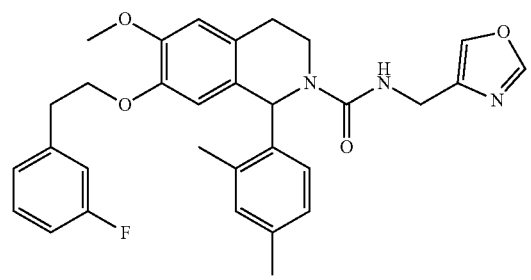
22
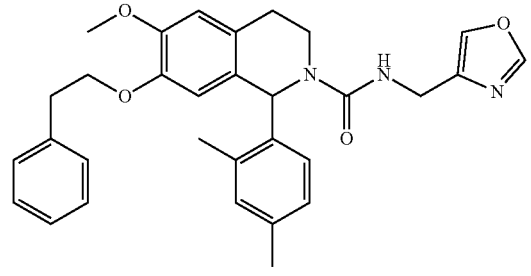
23
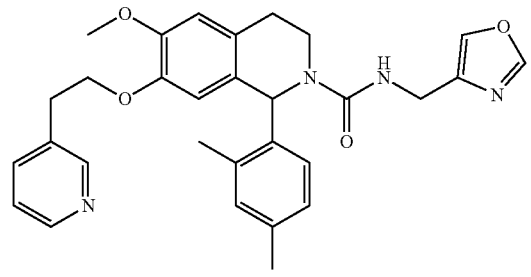
24
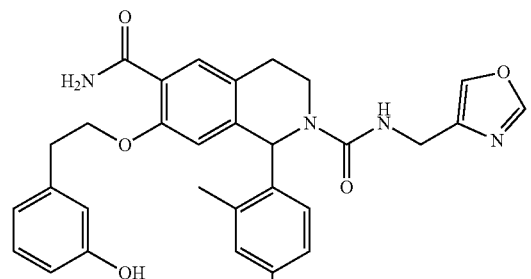
25
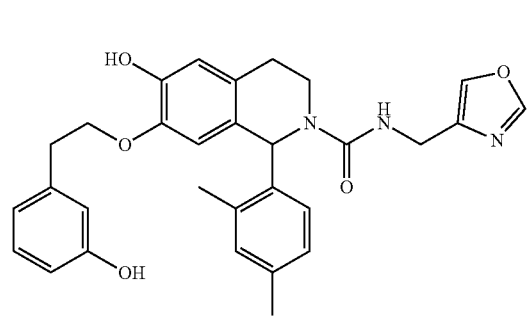

26
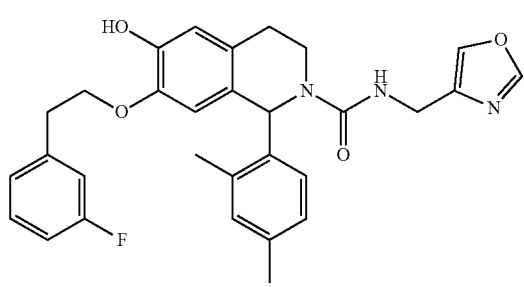
27
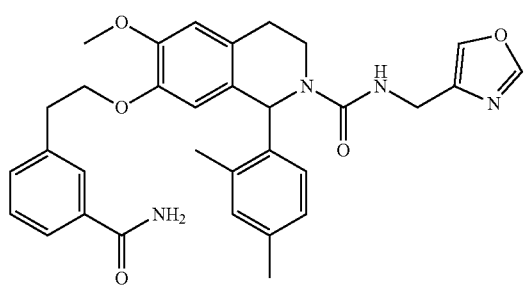
28
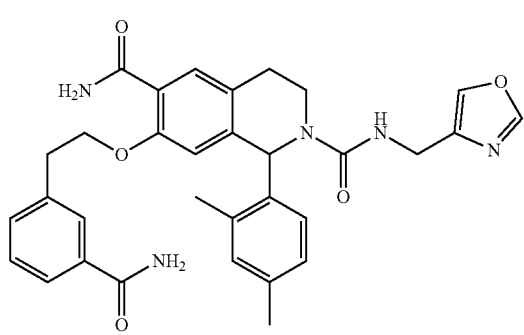
29
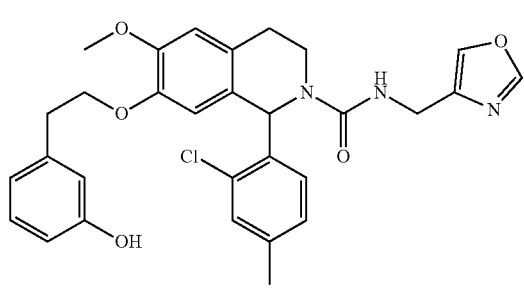
30
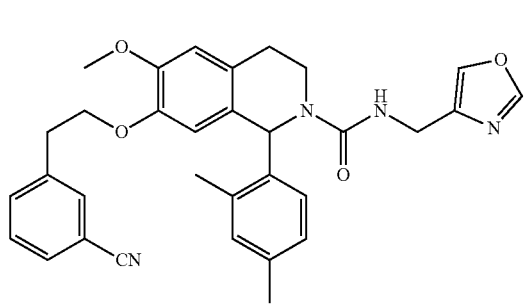
31
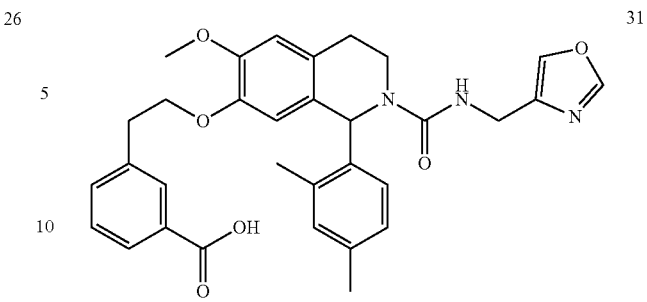
32
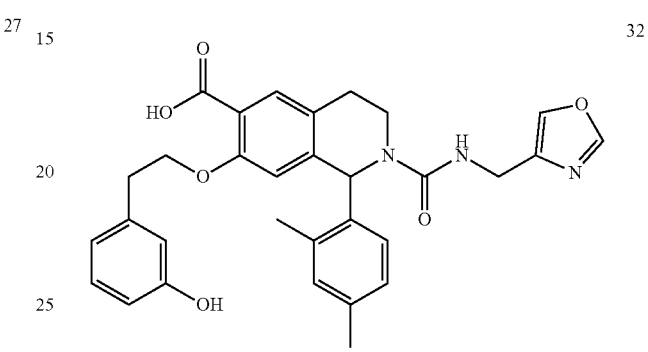
33
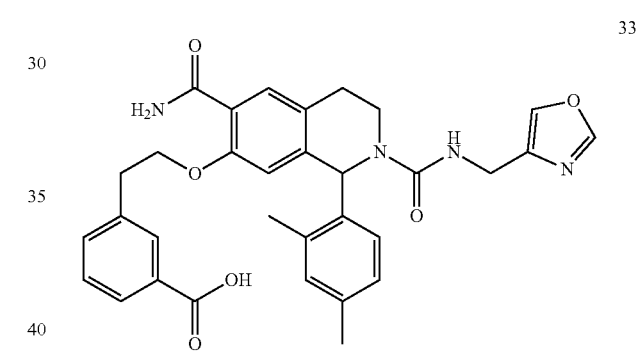
34
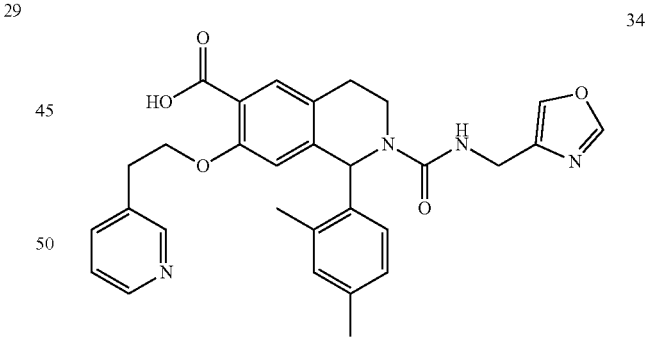
35
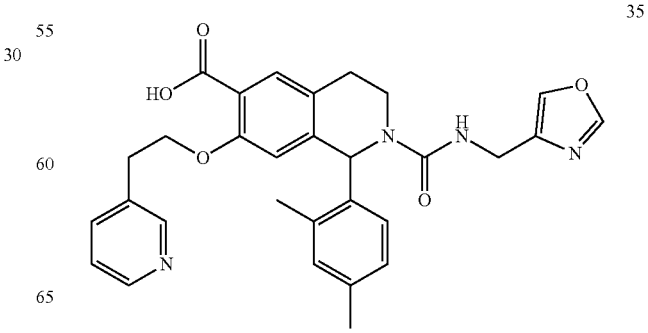

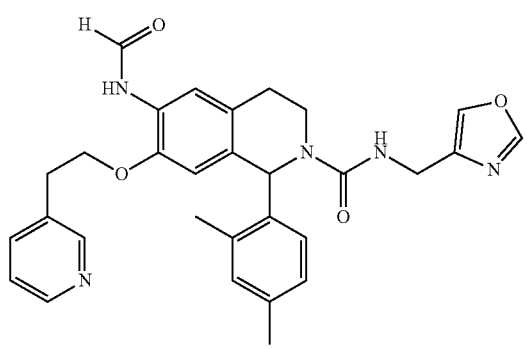
36
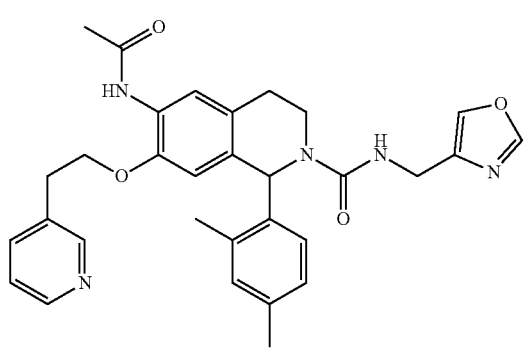
37
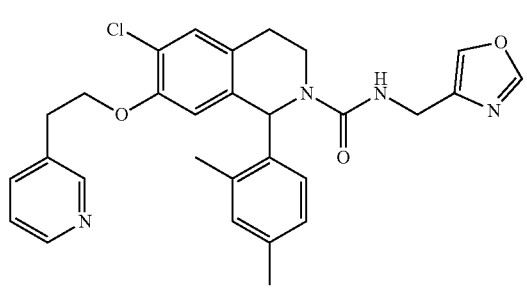
38
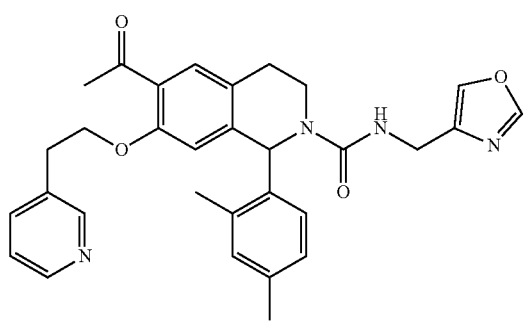
39
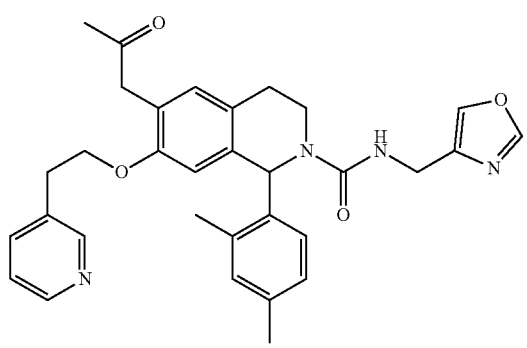
40
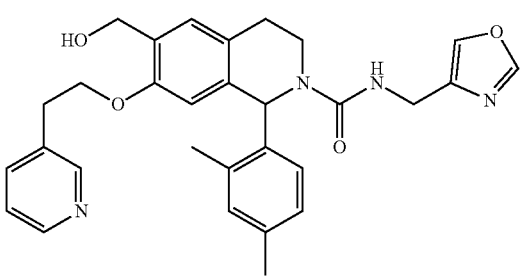
41
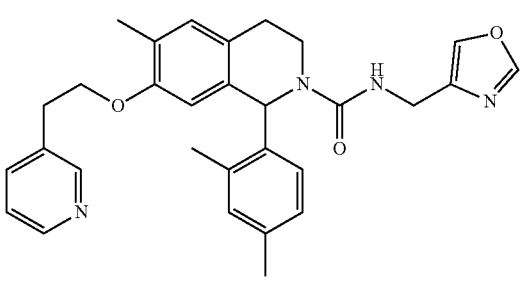
42
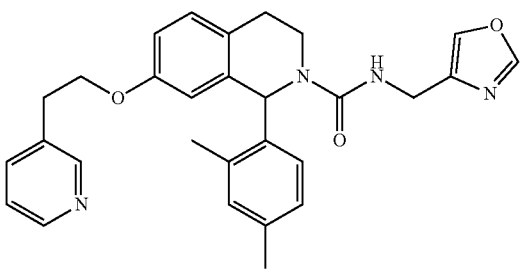
43
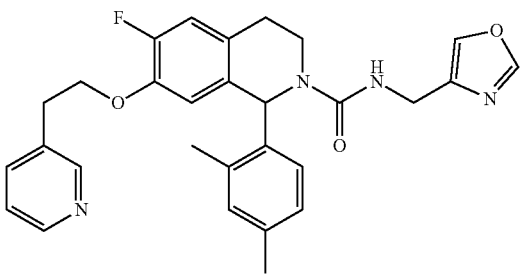
44
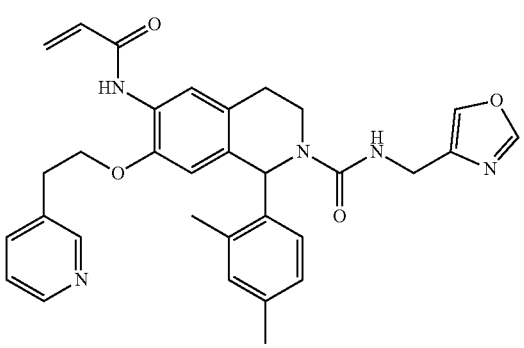
45

46
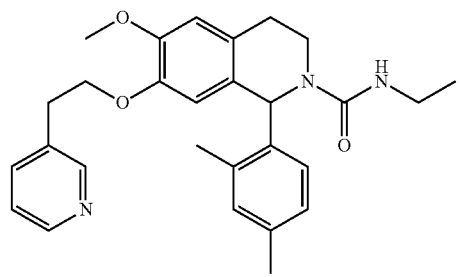
47
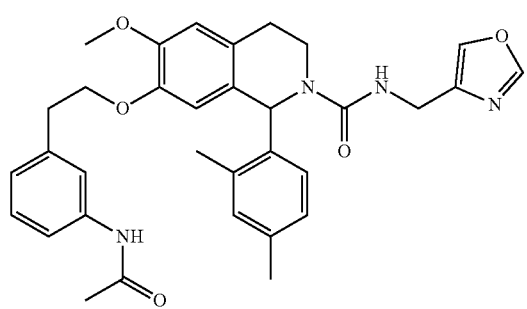
48
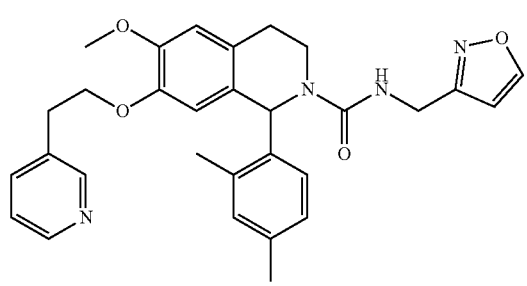
49
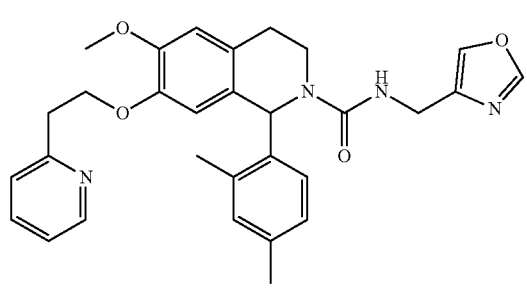
50
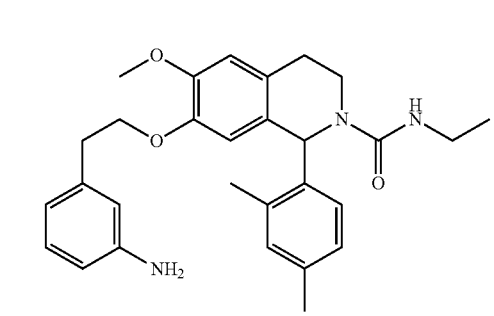
51
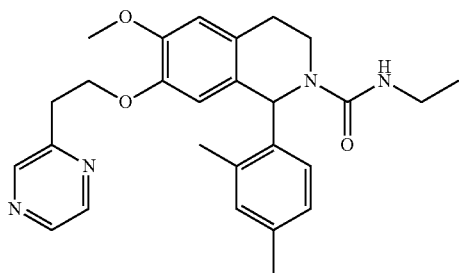
52
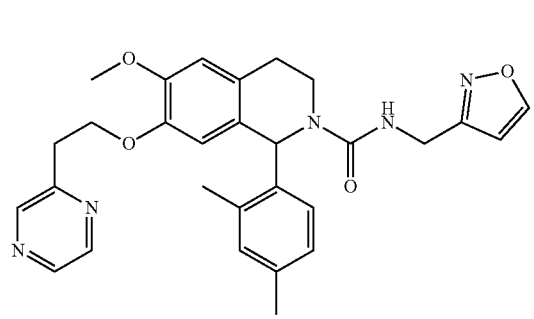
53
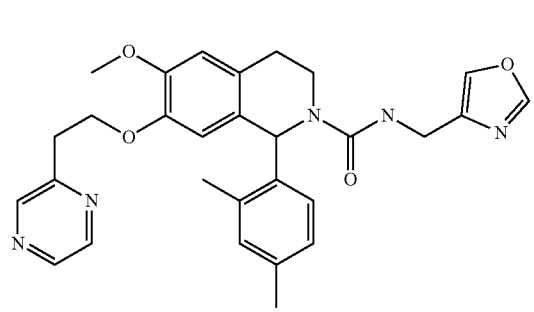
54
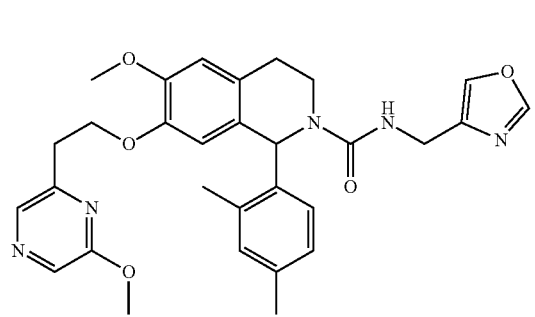
55
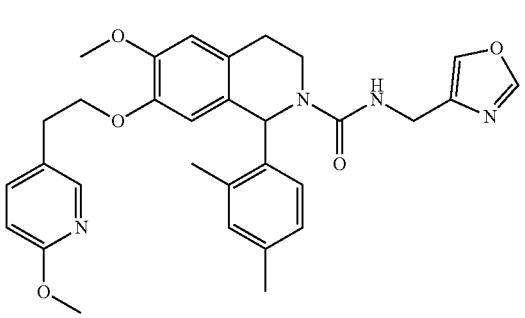

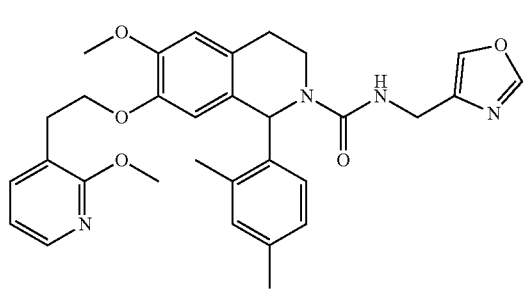

56

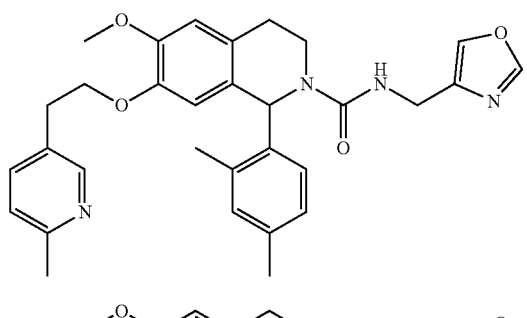

57

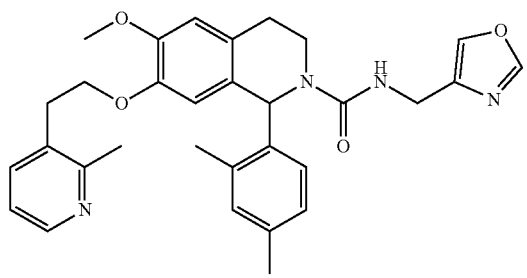

58

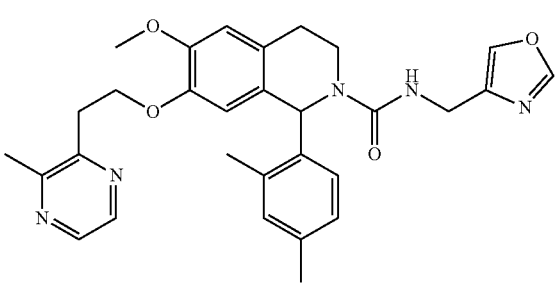

59

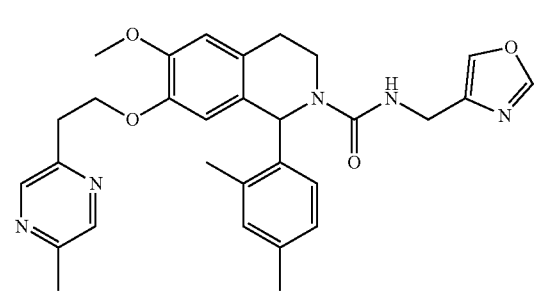

60

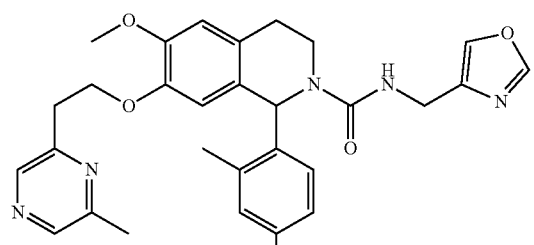

61

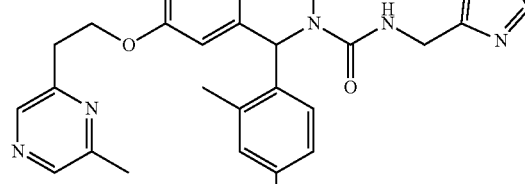

62

63

13. A pharmaceutical composition comprising at least one compound according to claim 1 and a pharmaceutically acceptable carrier.

14. A method for treatment of colon cancer, pancreatic cancer, multiple myeloma, and lung cancer associated with KRAS mutations in a subject in need thereof, comprising administering the pharmaceutical composition of claim 13 to the subject.

* * * * *

UNITED STATES PATENT AND TRADEMARK OFFICE
CERTIFICATE OF CORRECTION

Page 1 of 2

PATENT NO. : 11,466,012 B2
APPLICATION NO. : 16/961190
DATED : October 11, 2022
INVENTOR(S) : Vega García et al.

It is certified that error appears in the above-identified patent and that said Letters Patent is hereby corrected as shown below:

In the Claims

Column 58, Claim 12, Structure 33 is:

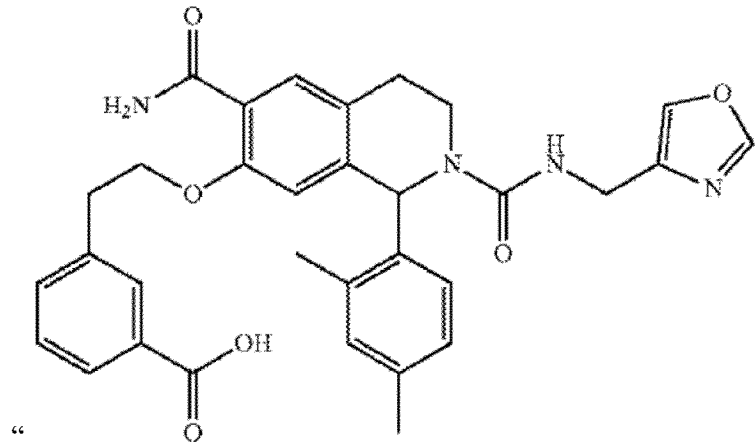

Signed and Sealed this
Thirteenth Day of January, 2026

John A. Squires
*Director of the United States Patent and Trademark Office*

CERTIFICATE OF CORRECTION (continued)
U.S. Pat. No. 11,466,012 B2

The structure should read:

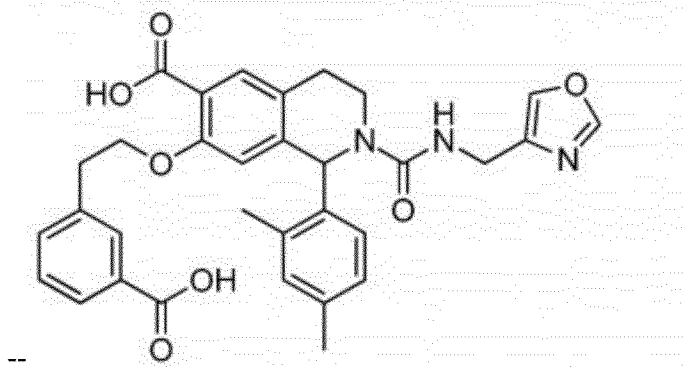

Column 58, Claim 12, Structure 34 is:

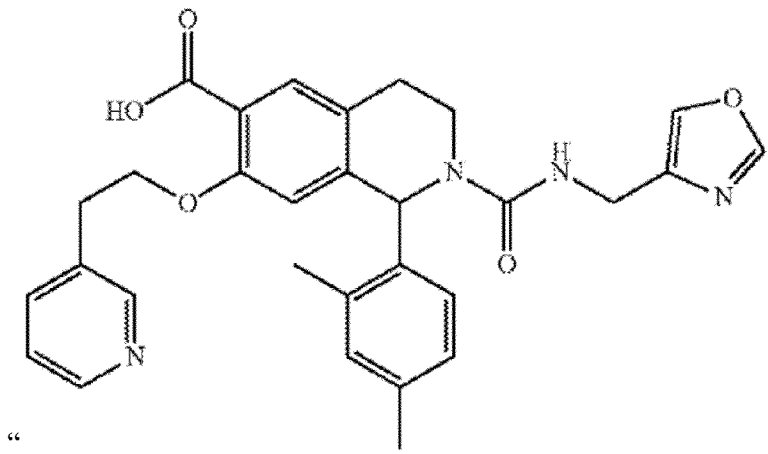

The structure should read: